United States Patent [19]

Mochizuki et al.

[11] Patent Number: 5,621,142
[45] Date of Patent: Apr. 15, 1997

[54] AMINOALKYLCYCLOPROPANE DERIVATIVES

[75] Inventors: Daisuke Mochizuki, Shizuoka-ken; Satoshi Shuto, Sapporo, both of Japan

[73] Assignee: Asahi Kasei Kogyo Kabushiki Kaisha, Osaka, Japan

[21] Appl. No.: 682,776

[22] PCT Filed: Feb. 22, 1995

[86] PCT No.: PCT/JP95/00254

§ 371 Date: Jul. 30, 1996

§ 102(e) Date: Jul. 30, 1996

[87] PCT Pub. No.: WO95/22521

PCT Pub. Date: Aug. 24, 1995

[30] Foreign Application Priority Data

Feb. 22, 1994 [JP] Japan .................................. 6-024513

[51] Int. Cl.⁶ .................................................. C07C 233/58
[52] U.S. Cl. ............................................ 564/164; 564/163
[58] Field of Search ........................................ 564/163, 164

[56] References Cited

U.S. PATENT DOCUMENTS 4,478,836 10/1984 Mouzin et al. ......................... 564/163

FOREIGN PATENT DOCUMENTS 3-56415 3/1991 Japan .

OTHER PUBLICATIONS

"Biochemical Profile of Midalcipran (F 2207), 1–Phenyl–1–Diethyl–Aminocarbonyl–2–Aminomethyl–Cyclopropane (Z) Hydrochloride, a Potential Fourth Generation Antidepressant Drug", *Neuropharmacology*, vol. 24, No. 12, 1985, pp. 1211–1219.

*Primary Examiner*—Shailendra Kumar
*Attorney, Agent, or Firm*—Young & Thompson

[57] ABSTRACT

Disclosed are a novel optically active compound represented by formula (1), a racemic modification thereof, and a pharmaceutically acceptable acid addition salt of the optically active compound or racemic modification thereof:

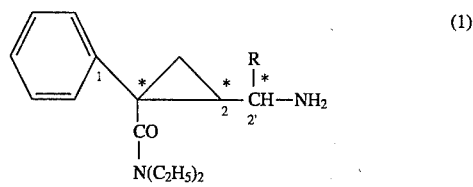

wherein R is a straight chain or branched $C_1$–$C_5$ aliphatic group which is saturated or unsaturated, or a phenyl group which is unsubstituted or substituted with 1 to 3 substituents which are each independently selected from the group consisting of a halogen atom, a $C_1$–$C_4$ alkyl group, a nitro group, an amino group, a hydroxyl group and a $C_1$–$C_4$ alkoxy group; and mark * indicates an asymmetric carbon atom.

The novel optically active aminoalkylcyclopropane derivative of the present invention, a racemic modification thereof, and a pharmaceutically acceptable acid addition salt of the optically active aminoalkylcyclopropane derivative or racemic modification thereof have remarkably high antagonistic activity with respect to NMDA receptor, as compared to known aminomethylcyclopropane derivatives and is useful as a preventive agent for cerebral infarction and a protective agent against ischemic diseases.

3 Claims, No Drawings

AMINOALKYLCYCLOPROPANE DERIVATIVES

This application is a 371 of PCT/JP95/00254 filed Feb. 22, 1995.

BACKGROUND OF THE INVENTION

1. Field of the Invention

The present invention relates to a novel aminoalkylcyclopropane derivative having an antagonistic activity with respect to N-methyl-D-aspartic acid (hereinbelow, referred to as "NMDA") receptor. More particularly, the present invention is concerned with a novel optically active aminoalkylcyclopropane derivative, a racemic modification thereof, or a pharmaceutically acceptable acid addition salt of the optically active aminoalkylcyclopropane derivative or racemic modification thereof, which has remarkably high antagonistic activity with respect to NMDA receptor, as compared to known aminomethylcyclopropane derivatives and is useful as a preventive agent for cerebral infarction and a protective agent against ischemic diseases.

2. Discussion of Related Art

It has been known that 1-phenyl-2-aminomethylcyclopropane derivatives, such as 1-phenyl-1-diethylaminocarbonyl-2-aminomethyl-cyclopropane hydrochloride (common name: Milnacipran) [hereinafter, referred to as "compound (A)"], represented by the following formula (A):

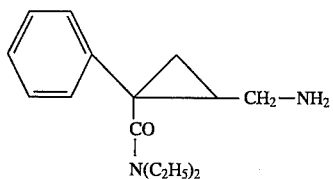

are useful for treating central nervous system neuropathy, and especially effective for treating neurotic depression and psychogenic neurosis (Examined Japanese Patent Application Publication No. 63-23186).

It has also been known that the above-mentioned compound (A) has an activity to inhibit the synaptosomal uptake of norepipephrine and 5-HT, which activity is known as anti-depression activity (Neuropharmacology, Vol. 24, No. 12, 1211–1219, 1985). It has also been known that the above-mentioned 1-phenyl-2-aminomethyl-cyclopropane derivative has an antagonistic activity with respect to NMDA receptor and is useful as a cell protective agent against ischemic brain cell damage (Unexamined Japanese Patent Application Laid-Open Specification No. 3-56415).

In the development of pharmaceutical products, it has been an important task to develop a compound having high antagonistic activity with respect to NMDA receptor, as compared to known compounds.

SUMMARY OF THE INVENTION

In order to solve the above-mentioned problem, the present inventors have made extensive and intensive studies on the steric structure characteristics of a cyclopropane ring. As a result, they have unexpectedly found that, when a specific organic group is introduced to the 2'-position of the cyclopropane ring of the known compound (A) mentioned above, the resultant new optically active compound, a racemic modification thereof, and a pharmaceutically acceptable acid addition salt of the optically active compound and racemic modification thereof, exhibit extremely high antagonistic activity with respect to NMDA receptor, as compared to known compounds. The present invention has been completed, based on this novel finding.

Accordingly, it is an object of the present invention to provide a novel compound having high antagonistic activity with respect to NMDA receptor, as compared to known compounds.

DETAILED DESCRIPTION OF THE INVENTION

According to the present invention, there is provided an optically active compound represented by formula (1), a racemic modification thereof, or a pharmaceutically acceptable acid addition salt of the optically active compound or racemic modification thereof:

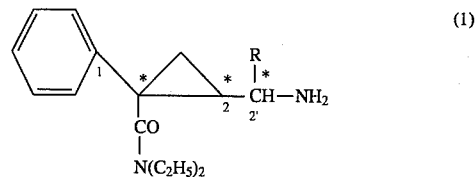

wherein R is a straight chain or branched $C_1$–$C_5$ aliphatic group which is saturated or unsaturated, or a phenyl group which is unsubstituted or substituted with 1 to 3 substituents which are each independently selected from the group consisting of a halogen atom, a $C_1$–$C_4$ alkyl group, a nitro group, an amino group, a hydroxyl group and a $C_1$–$C_4$ alkoxy group; and mark * indicates an asymmetric carbon atom.

The respective meanings of the abbreviations used in the present specification are as follows:

Ph: phenyl group

Me: methyl group

Et: ethyl group

Piv: pivaloyl group

Tos: tosyl group

Boc: t-butoxycarbonyl group.

In the present specification, a positional numbers in a compound are in accordance with the positional numbers indicated in formula (1).

In the above-mentioned formula (1), R is a straight chain or branched $C_1$–$C_5$ aliphatic group which is saturated or unsaturated, or a phenyl group which is unsubstituted or substituted with 1 to 3 substituents which are each independently selected from the group consisting of a halogen atom, a $C_1$–$C_4$ alkyl group, a nitro group, an amino group, a hydroxyl group and a $C_1$–$C_4$ alkoxy group. Examples of aliphatic groups include an alkyl group, an alkenyl group and an alkynyl group. Examples of alkyl groups include a methyl group, an ethyl group, a propyl group, an isopropyl group, a butyl group and an isobutyl group. Examples of alkenyl groups include a vinyl group, an allyl group and an isopropenyl group. Examples of alkynyl groups include an ethynyl group, a 1-propynyl group and a 2-propynyl group. Among aliphatic groups, a methyl group and an ethyl group are especially preferred. Among unsubstituted or substituted phenyl groups, a phenyl group is especially preferred.

As is apparent from formula (1), the compound of the present invention has 3 asymmetric carbon atoms at the 1-, 2- and 2'-positions and, therefore, the compound of the present invention includes 8 different types of optically active compounds. Examples of such optically active compounds include (1S, 2R, 2'S), (1S, 2R, 2'R), (1R, 2S, 2'R)

and (1R, 2S, 2'S) forms of optically active compounds and racemic modifications thereof. Especially when R represents a lower aliphatic group, a (1S, 2R, 2'S) form of optically active compound and a racemic modification thereof are preferred.

Examples of the above-mentioned pharmaceutically acceptable acid addition salts include a salt with an inorganic acid, such as hydrochloric acid, sulfuric acid and phosphoric acid; and a salt with an organic acid, such as acetic acid, propionic acid, succinic acid, malic acid, tartaric acid, citric acid, glycolic acid, fumaric acid, methanesulfonic acid, p-toluenesulfonic acid, aspartic acid and glutamic acid.

The compound of the present invention represented by formula (1) can be produced, for example, by the following method.

First, epichlorohydrin is reacted with phenylacetonitrile in a reaction solvent containing a strongly basic reagent. The resultant product is hydrolyzed, and the hydrolysate is treated with an acid to thereby obtain a lactone [hereinafter, referred to as "lactone (2)"] represented by the following formula (2):

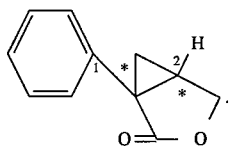

The obtained lactone (2) is reacted with lithium diethylamide in a reaction solvent to thereby obtain a hydroxymethyl [hereinafter, referred to as "hydroxymethyl (3)"] represented by the following formula (3):

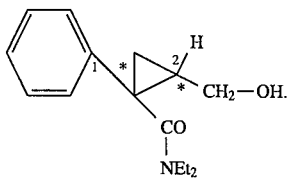

The obtained hydroxymethyl (3) is oxidized in a reaction solvent by an oxidation method, such as Swern oxidation, Moffatt oxidation or chromic acid oxidation method, to thereby obtain an aldehyde [hereinafter, referred to as "aldehyde (4)"] represented by the following formula (4):

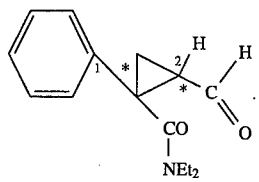

The obtained aldehyde (4) is reacted in a reaction solvent with an organometallic reagent, such as Grignard reagent, to thereby obtain an alcohol [hereinafter, referred to as "alcohol (5)"] represented by the following formula (5):

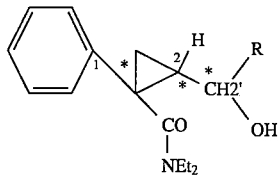

wherein R is as defined for formula (1).

The obtained alcohol (5) is reacted with $NaN_3$ in a reaction solvent in the presence of triphenylphosphine and carbon tetrahalide to thereby obtain an azide [hereinafter, referred to as "azide (6)"] represented by the following formula (6):

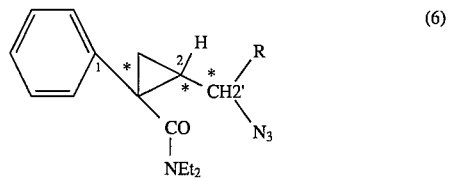

wherein R is as defined for formula (1).

Finally, the obtained azide (6) is subjected to catalytic reduction in a reaction solvent in the presence of a reduction catalyst and in a hydrogen gas atmosphere of 1 to 5 arm to thereby obtain the desired compound (1).

In the reaction of epichlorohydrin with phenylacetonitrile for obtaining lactone (2), epichlorohydrin is used in an amount of from 0.2 to 2 equivalents per equivalent of phenylacetonitrile. The reaction is conducted at a temperature of from −80° C. to 50° C. for a period of from 0.5 hour to 50 hours. Examples of reaction solvents include tetrahydrofuran (THF), diethyl ether, benzene, toluene, hexane, N,N-dimethylformamide (DMF) and dimethyl sulfoxide (DMSO). It is preferred that the reaction solvent be used in an amount which is 5 to 50 times the weight of phenylacetonitrile. Examples of strongly basic reagents include sodium amide, sodium hydride, butyllithium and lithium diisopropylamide. It is preferred that the above-mentioned reaction be conducted under anhydrous conditions and that the reaction be conducted in a stream of inert gas, such as argon gas.

The reaction product obtained by the above-mentioned reaction of epichlorohydrin with phenylacetonitrile, i.e. 1-phenyl-1-cyano-2-hydroxymethylcyclopropane, is hydrolyzed with an aqueous alkali solution, which is used in an amount of from 1 to 30 equivalents per equivalent of the reaction product, in a reaction solvent, such as ethanol, to thereby obtain a hydrolysate. The hydrolysate is treated with an excess amount of acid to thereby obtain the desired lactone (2). The above-mentioned hydrolysis is conducted at a temperature of from 0° C. to 100° C., preferably under heating, for a period of from 0.5 hour to 50 hours. Also, the acid treatment after the hydrolysis is conducted at a temperature of from 0° C. to 100° C. for a period of from 0.5 hour to 50 hours. Examples of aqueous alkali solutions to be used in the above-mentioned hydrolysis include aqueous solutions of alkali hydroxides, such as potassium hydroxide and sodium hydroxide. By the above-mentioned hydrolysis, the nitrile moiety of the compound is hydrolyzed to form 1-phenyl-2-hydroxymethylcyclopropane carboxylic acid. By the above-mentioned acid treatment, the hydrolysate is lactonized. Examples of acids to be used in the acid treatment include known inorganic acids, such as hydrochloric acid, sulfuric acid and the like.

Lithium diethylamide to be used in the reaction for obtaining hydroxymethyl (3) from lactone (2) can be prepared by reacting diethylamine with butyllithium. Lithium diethylamide is used in an amount which is 1 to 10 times the weight of lactone (2). The reaction is generally conducted at a temperature of from −100° C. to room temperature, preferably at a temperature of 0° C. or lower, for a period of from 0.5 hour to 10 hours. Examples of reaction solvents to be used in the reaction include tetrahydrofuran (THF), diethyl ether, toluene, hexane, dimethylformamide (DMF), dimethyl sulfoxide (DMSO) and dichloromethane. The reaction solvent is used in an amount which is 5 to 50 times the weight of lactone (2). It is preferred that the above-mentioned reaction be conducted under anhydrous conditions and that the reaction be conducted in a stream of inert gas, such as argon gas.

Examples of reaction solvents to be used in the reaction for obtaining aldehyde (4) from hydroxymethyl (3) include known inert solvents usable in oxidation reactions, and the reaction solvent is used in an amount which is 5 to 50 times the weight of hydroxymethyl (3). An oxidizing agent to be used in the oxidation of hydroxymethyl (3) may be appropriately selected depending on the oxidation method. The oxidizing agent is used in an amount of from 1 to 10 equivalents per equivalent of hydroxymethyl (3). Examples of combinations of oxidation method and oxidizing agent include Swern oxidation method wherein DMSO is used as the oxidizing agent, Moffatt oxidation method wherein DMSO is used as the oxidizing agent, and chromic acid oxidation method wherein pyridinium chlorochromate or pyridinium dichromate is used as the oxidizing agent. A preferred example of oxidation method is Swern oxidation method wherein hydroxymethyl (3) is treated with oxalyl chloride or DMSO and then with a base, such as triethylamine. The above-mentioned reaction is conducted at a temperature of from −100° C. to room temperature, preferably at a temperature of 0° C. or lower, for a period of from 0.5 hour to 10 hours.

Examples of reaction solvents to be used in the reaction for obtaining alcohol (5) from aldehyde (4) include THF, diethyl ether, toluene, hexane, DMF and DMSO. The reaction solvent is used in an amount which is 5 to 50 times the weight of aldehyde (4). In the reaction, an organometallic reagent, such as Grignard reagent, is used in order to introduce an R group defined in formula (1) to the 2'-position of aldehyde (4). Examples of such Grignard reagents include lower aliphatic hydrocarbon MgBr, such as lower alkyl MgBr (methyl MgBr, ethyl MgBr, propyl MgBr, isopropyl MgBr, butyl MgBr, isobutyl MgBr and the like), lower alkenyl MgBr and lower alkynyl MgBr; and phenyl MgBr such as phenyl MgBr which is unsubstituted or substituted. Examples of organometallic reagents other than Grignard reagent include known organometallic reagents which can be bonded to a carbonyl group by an addition reaction, such as organolithium, organoaluminum, organotitanium and organozinc, each of which is substituted with an organic substituent, such as a lower aliphatic hydrocarbon group, e.g., lower alkyl (methyl, ethyl, propyl, isopropyl, butyl, isobutyl and the like), lower alkenyl and lower alkynyl. Organometallic reagents, such as Grignard reagent, is used in an amount of from 1 to 10 equivalents per equivalent of aldehyde (4). It is preferred that the above-mentioned reaction be conducted under anhydrous conditions and that the reaction be conducted in a stream of inert gas, such as argon gas. The reaction is conducted at a temperature of from −100° C. to room temperature, preferably at a temperature of 0° C. or lower, for a period of from 0.5 hour to 10 hours.

Examples of reaction solvents to be used in the reaction for obtaining azide (6) from alcohol (5) include an aprotic solvent, and the reaction solvent is used in an amount which is 5 to 50 times the weight of alcohol (5). Examples of carbon tetrahalides include carbon tetrabromide, carbon tetrachloride and carbon tetraiodide. In the reaction, each of triphenylphosphine and carbon tetrahalide is used in an amount of from 1 to 10 equivalents per equivalent of alcohol (5), and $NaN_3$ is used in an amount of from 1 to 100 equivalents per equivalent of alcohol (5). The above-mentioned reaction is conducted at a temperature of from −20° C. to 100° C. preferably at room temperature, for a period of from 0.5 hour to 50 hours.

The reaction solvent to be used in the reaction for obtaining the desired compound (1) from azide (6) can be selected from various known solvents usable in a catalytic reduction. Preferable examples of reaction solvents include ethyl acetate, hexane, methanol, ethanol and THF. The reaction solvent is used in an amount which is 5 to 50 times the weight of azide (6). Examples of reduction catalysts include metal catalysts such as Pd, Ni and Pt. Preferable examples of metal catalysts include a mixture of Pd and carbon (Pd/C). The catalyst may be used in an amount of from 0.001 to 1 equivalent per equivalent of azide (6). The reducing reaction is generally conducted at a temperature of from −20° C. to 50° C. for a period of from 0.5 hour to 50 hours.

In the above-mentioned process wherein, using epichlorohydrin as a starting material, the desired compound (1) is obtained through intermediate compounds (2), (3), (4), (5) and (6), when (R)-(−)-epichlorohydrin is used as a starting material, the desired compound (1) is a (1S, 2R, 2'S) form of optically active compound (1) [hereinafter, referred to as "compound (1a)"] represented by the following formula (1a):

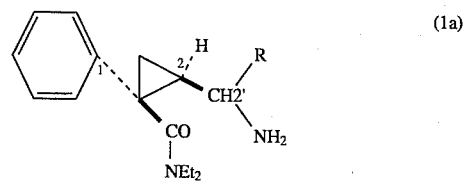

wherein R is as defined for formula (1). When (S)-(+)-epichlorohydrin is used as a starting material, the desired compound (1) is a (1R, 2S, 2'R) form of optically active compound (1) [hereinafter, referred to as "compound (1c)"] represented by the following formula (1c):

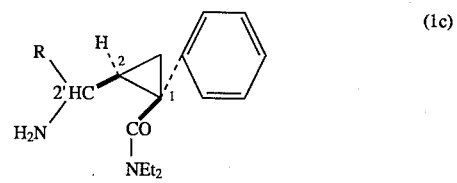

wherein R is as defined for formula (1). When racemic modifications of the above-mentioned (R)-(−)- and (S)-(+)-epichlorohydrins are used as starting materials, racemic modifications of compounds (1a) and (1c) are obtained as desired compounds.

Therefore, when (R)-(−)-epichlorohydrin is used as a starting material, the intermediate products, lactone (2), hydroxymethyl (3) and aldehyde (4), are optically active compounds of (1S, 2R) form, and the intermediate products, alcohol (5) and azide (6), are optically active compounds of (1S, 2R, 2'S) form. When (S)-(+)-epichlorohydrin is used as a starting material, the intermediate products, lactone (2), hydroxymethyl (3) and aldehyde (4), are optically active compounds of (1R, 2S) form, and the intermediate products, alcohol (5) and azide (6), are optically active compounds of (1R, 2S, 2'R) form.

The compound of the present invention represented by formula (1) can also be produced via the following reaction route.

Specifically, alcohol (5) produced in the above-mentioned process is oxidized in a reaction solvent by an oxidation method, such as Swern oxidation, Moffatt oxidation or chromic acid oxidation method, to thereby obtain a ketone [hereinafter, referred to as "ketone (7)"] represented by the following formula (7):

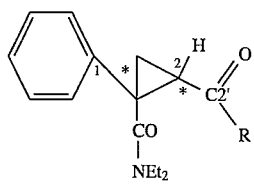

(7)

wherein R is as defined for formula (1).

The obtained ketone (7) is subjected to reduction, in a reaction solvent, with a reducing agent which is capable of reducing ketone to alcohol, to thereby obtain an alcohol [hereinafter, referred to as "alcohol (8)"] represented by the following formula (8):

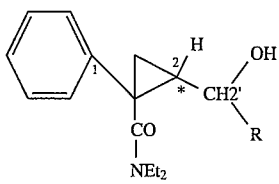

(8)

wherein R is as defined for formula (1).

The obtained alcohol (8) is reacted with NaN₃ in a reaction solvent in the presence of triphenylphosphine and carbon tetrahalide to thereby obtain an azide [hereinafter, referred to as "azide (9)"] represented by the following formula (9):

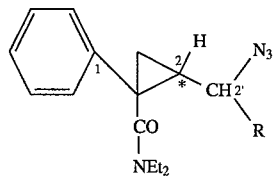

(9)

wherein R is as defined for formula (1).

The obtained azide (9) is subjected to catalytic reduction, in a reaction solvent, with a reduction catalyst in a stream of hydrogen gas to thereby obtain the desired compound (1).

Examples of reaction solvents to be used in the reaction for obtaining ketone (7) from alcohol (5) include conventional inert solvents usable in oxidation reactions. An oxidizing agent to be used in the oxidation of alcohol (5) may be appropriately selected depending on the oxidation method. The oxidizing agent is used in an amount of from 1 to 10 equivalents per equivalent of alcohol (5). Examples of combinations of oxidation method and oxidizing agent include Swern oxidation method wherein DMSO is used as the oxidizing agent, Moffatt oxidation method wherein DMSO is used as the oxidizing agent, and chromic acid oxidation method wherein pyridinium chlorochromate or pyridinium dichromate is used as the oxidizing agent. Among them, preferred is chromic acid oxidation method wherein pyridinium dichromate is used as the oxidizing agent. The above-mentioned reaction is conducted at a temperature of from −100° C. to room temperature for a period of from 0.5 hour to 10 hours.

Examples of reaction solvents to be used in the reaction for obtaining alcohol (8) from ketone (7) include inert solvents, such as THF, which are unsusceptible to reduction. The reaction solvent may be used in an amount which is 5 to 50 times the weight of ketone (7). Examples of reducing agents capable of reducing ketone to alcohol include boron-containing reducing agents and aluminum-containing reducing agents, such as BH₃, NaBH₄, LiAlH₄, DIBALH (diisobutylaluminumhydride) and NaBH₃CN; and reduction catalysts, such as Pd, Pt and Ni. The reducing agent may be used in an amount of from 1 to 10 equivalents per equivalent of ketone (7). The above-mentioned reaction is generally conducted at a temperature of from −100° C. to room temperature for a period of from 0.5 hour to 50 hours.

The reaction for obtaining azide (9) from alcohol (8) can be conducted in the same manner as in the above-mentioned reaction for obtaining azide (6) from alcohol (5). The reaction for obtaining the desired compound (1) from azide (9) can be conducted in the same manner as in the reaction for obtaining the desired compound (1) from azide (6).

In the above-mentioned process wherein, using epichlorohydrin as a starting material, the desired compound (1) is obtained through intermediate compounds (2), (3), (4), (5), (7), (8) and (9), when (R)-(−)-epichlorohydrin is used as a starting material to produce lactone (2), the desired compound (1) is a (1S, 2R, 2'R) form of optically active compound (1) [hereinafter, referred to as "compound (1b)"] represented by the following formula (1b):

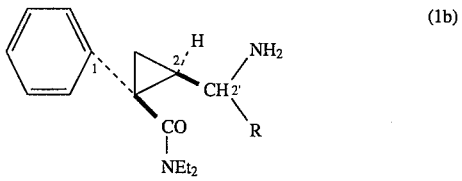

(1b)

wherein R is as defined for formula (1). When (S)-(+)-epichlorohydrin is used as a starting material, the desired compound (1) is a (1R, 2S, 2'S) form of optically active compound (1) [hereinafter, referred to as "compound (1d)"] represented by the following formula (1d):

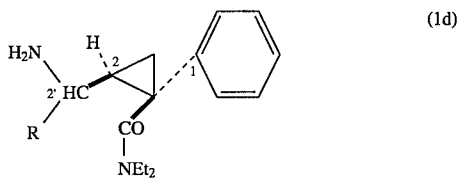

(1d)

wherein R is as defined for formula (1).

When racemic modifications of the above-mentioned (R)-(−)- and (S)-(+)-epichlorohydrins are used as starting materials, racemic modifications of compounds (1b) and (1d) are obtained as desired compounds.

Therefore, when (R)-(−)-epichlorohydrin is used as a starting material, the intermediate products, alcohol (8) and azide (9), are optically active compounds of (1S, 2R, 2'R) form. When (S)-(+)-epichlorohydrin is used as a starting material, the intermediate products, alcohol (8) and azide (9), are optically active compounds of (1R, 2S, 2'S) form.

When a desired compound (1) wherein R in formula (1) is an unsaturated C₂–C₅ aliphatic group is produced by a process involving the step of reacting aldehyde (4) with a Grignard reagent so as to introduce an R group, there is a danger that unsaturated bonds in R are undesirably reduced at the step of reduction of azide (6) or (9). Such a danger can be removed by conducting the introduction of R by the following method: a group convertible into a desirable unsaturated aliphatic hydrocarbon group is introduced to aldehyde (4) to thereby obtain a derivative of aldehyde (4), and the derivative of aldehyde (4) is used instead of aldehyde (4) to obtain an azide through an alcohol or the like; the obtained azide is subjected to reduction to produce an amino compound as a precursor of the desired compound (1); and then the introduced convertible group in the amino compound is converted into the desired unsaturated aliphatic hydrocarbon group to thereby obtain the desired compound (1).

For example, compound (1) having a vinyl group as R of formula (1) can be produced via the following reaction route.

Aldehyde (4) obtained in the above-mentioned manner is reacted in a reaction solvent, such as THF, with a lithium-containing lower alkyl ester of acetic acid, such as ethoxycarbonylmethyllithium to thereby obtain an alcohol [hereinafter, referred to as "alcohol (10)"] represented by the following formula (10):

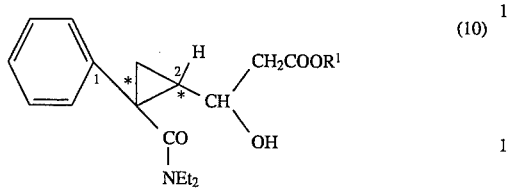

(10)

wherein $R^1$ represents a lower alkyl group.

The obtained alcohol (10) is subjected to reduction by $NaBH_4$ in a reaction solvent composed of a lower alcohol, such as methanol, to thereby obtain a diol [hereinafter, referred to as "diol (11)"] represented by the following formula (11):

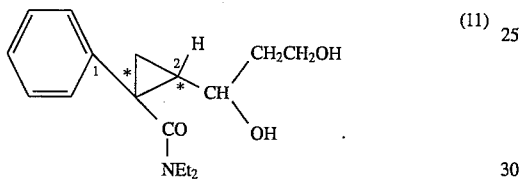

(11)

The obtained diol (11) is reacted in a reaction solvent with a protecting agent containing a hydroxyl-protecting group, such as a pivaloyl group, which is capable of selectively protecting a primary hydroxyl group, to thereby protect a hydroxyl group at the 3-position of diol (11) and then, further reacted with $NaN_3$ in a reaction solvent containing triphenylphosphine and carbon tetrahalide to thereby obtain an azide [hereinafter, referred to as "azide (12)"] represented by the following formula (12):

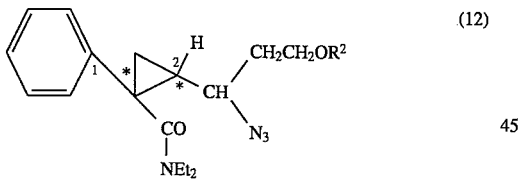

(12)

wherein $R^2$ represents a hydroxyl-protecting group.

The hydroxyl-protecting group is removed from azide (12) and then, the hydroxyl group of azide (12) is sulfonylated with a sulfonyl halide, such as methanesulfonyl halide or toluenesulfonyl halide, in a reaction solvent, such as dichloromethane and chloroform, containing a tertiary organic amine, such as triethylamine or dimethylaminopyridine, to thereby obtain an azide [hereinafter, referred to as "azide (13)"] represented by the following formula (13):

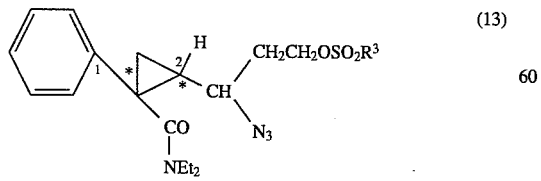

(13)

wherein $R^3$ represents an organosulfonyl group.

The obtained azide (13) is reacted in a reaction solvent with a reaction product between diphenyl diselenide and $NaBH_4$ to thereby phenylselenylate the organosulfonyloxy group of azide (13) and obtain an azide [hereinafter, referred to as "azide (14)"] represented by the following formula (14):

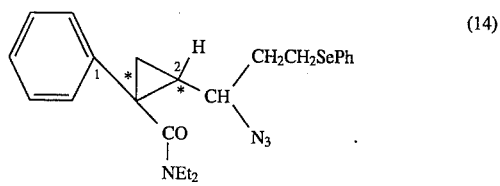

(14)

The obtained azide (14) is reacted with triphenylphosphine in pyridine and then with 28% aqueous ammonia to thereby obtain an amino compound [hereinafter, referred to as "amino compound (15)"] represented by the following formula (15):

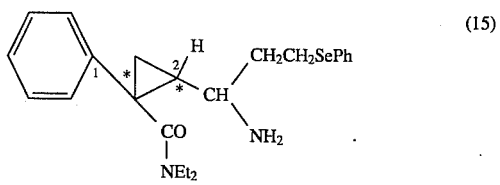

(15)

The obtained amino compound (15) is reacted with a known reagent containing an amino-protecting group, such as t-butoxycarbonyl group which can be removed by acid treatment, to thereby protect the amino group of amino compound (15) by the protecting group and obtain a selenyl compound [hereinafter, referred to as "selenyl compound (16)"] represented by the following formula (16):

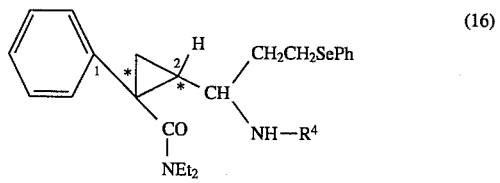

(16)

wherein $R^4$ represents an amino-protecting group.

The obtained selenyl compound (16) is reacted with hydrogen peroxide in a reaction solvent, such as THF, to thereby effect oxidation-removal of the phenylselenyl group and obtain a protected amino compound [hereinafter, referred to as "protected amino compound (17)"] represented by the following formula (17):

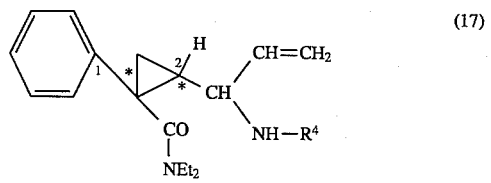

(17)

wherein $R^4$ represents an amino-protecting group.

The amino-protecting group of protected amino compound (17) is removed by a conventional method to thereby obtain the desired compound (1) wherein R of formula (1) is a vinyl group.

A lithium-containing lower alkyl ester of acetic acid to be reacted with aldehyde (4) can be produced by the following method. For example, ethoxycarbonylmethyllithium can be prepared by a method comprising: mixing hexamethyldisilazane and THF to thereby obtain a mixture, adding to the mixture a hexane solution of butyllithium in a stream of argon gas, and adding thereto anhydrous ethyl acetate while cooling with dry ice as a refrigerant. The lithium-containing lower alkyl ester of acetic acid, such as ethoxycarbonylmethyllithium, can be used in an amount of from 1 to 20 equivalents per equivalent of aldehyde (4).

The reaction for obtaining alcohol (10) from aldehyde (4) is generally conducted at a temperature of from −80° C. to 0° C., preferably while cooling with dry ice in a stream of argon gas, for a period of from 0.5 hour to 10 hours. As a result of the above-mentioned reaction, 2 different types of alcohols (10) which have different sterical structure characteristics at the 2'-position are obtained, and they can be separated from each other by column chromatography using a carrier, such as silica gel.

When a (1S, 2R) form of optically active aldehyde (4) is used, 2 types of alcohols (10), namely, (1S, 2R, 2'S) and (1S, 2R, 2'R) forms of optically active compounds are obtained.

Examples of reaction solvents to be used in the reaction for obtaining diol (11) from alcohol (10) include lower alcohols, such as methanol, and the solvent may be used in an amount which is 5 to 50 times the weight of alcohol (10). $NaBH_4$ may be used in an amount of from 1 to 20 equivalents per equivalent of alcohol (10). The reaction may be conducted at a temperature of from −80° C. to reflux temperature for a period of from 0.5 hour to 30 hours, but the reaction can satisfactorily proceed at room temperature.

Examples of reaction solvents to be used in the reaction for protecting a hydroxyl group at the 3-position of diol (11) include anhydrous pyridine, and the reaction solvent may be used in an amount which is 5 to 50 times the weight of diol (11). Examples of protecting agents include pivaloyl chloride, and the protecting agent may be used in an amount of from 1 to 20 equivalents per equivalent of diol (11). The reaction may be conducted at a temperature of from −80° C. to reflux temperature for a period of from 0.5 hour to 30 hours, preferably in a stream of argon gas while cooling with ice.

The reaction for obtaining azide (12) from diol (11) having a protected hydroxyl group at the 3-position can be conducted in substantially the same manner as in the above-mentioned reaction for obtaining azide (6) from alcohol (5).

Removal of a hydroxyl-protecting group, such as a pivaloyl group, from azide (12) can be conducted by reacting sodium methoxide with azide (12) in a reaction solvent such as methanol, preferably in a stream of argon gas. The reaction is generally conducted at room temperature for a period of from 0.5 hour to 30 hours.

Preferable examples of organosulfonyl halides to be used in the organosulfonylation of a hydroxyl group of the alcohol obtained in the above-mentioned reaction include tosyl chloride. The organosulfonyl halide may be used in an amount of from 1 to 20 equivalents per equivalent of azide (12). In the reaction, the reaction solvent may be used in an amount which is 5 to 50 times the weight of azide (12), and a tertiary organic amine may be used in an amount which is 1 to 20 times the weight of azide (12). The reaction is conducted at a temperature of from −20° C. to reflux temperature for a period of from 0.5 hour to 30 hours, preferably in a stream of argon gas.

The method for producing azide (14) by phenylselenylation of azide (13) comprises dissolving diphenyl diselenide in a reaction solvent to thereby obtain a first solution, adding $NaBH_4$ to the obtained first solution to thereby obtain a second solution, and reacting azide (13) with the obtained second solution. It is preferred that the reaction be conducted in a stream of argon gas. Examples of reaction solvents to be used in the reaction for obtaining azide (14) by phenylselenylating azide (13) include lower alcohols, such as anhydrous ethanol, and the solvent may be used in an amount which is 5 to 50 times the weight of azide (13). In the reaction, the reaction product between diphenyl diselenide and $NaBH_4$ can be used in an amount of from 1 to 20 equivalents per equivalent of azide (13). The reaction may be conducted at a temperature of from −80° C. to reflux temperature for a period of from 0.5 hour to 30 hours, but can satisfactorily proceed at room temperature.

In obtaining amino compound (15) from azide (14), both of the reaction of azide (14) with triphenylphosphine, and the subsequent reaction of the resultant reaction product with aqueous ammonia may be conducted at a temperature of from −20° C. to 100° C. for a period of from 0.5 hour to 30 hours, but can satisfactorily proceed at room temperature. In those reactions, pyridine to be used as a reaction solvent may be used in an amount which is 5 to 50 times the weight of azide (14); triphenylphosphine may be used in an amount of from 1 to 20 equivalents per equivalent of azide (14); and aqueous ammonia may be used in an amount which is 1 to 100 times the weight of azide (14).

The protection of an amino group of amino compound (15) can be conducted in the same manner as in conventional methods for protecting amino groups. For example, the amino group can be protected by conducting a reaction of amino compound (15) with a protecting agent, such as di-t-butyl dicarbonate, which is used in an amount of from 1 to 20 equivalents per equivalent of amino compound (15), in a reaction solvent, such as anhydrous dichloromethane, which is used in an amount which is 5 to 50 times the weight of amino compound (15), at a temperature of from −20° C. to 100° C. for a period of from 0.5 hour to 30 hours.

In the oxidation of selenyl compound (16) for obtaining protected amino compound (17), a reaction solvent is used in an amount which is 5 to 50 times the weight of selenyl compound (16). Hydrogen peroxide is used in an amount of from 1 to 100 equivalents per equivalent of selenyl compound (16). The reaction may be conducted at a temperature of from −80° C. to 60° C. for a period of from 0.5 hour to 30 hours, and is generally conducted while heating.

The removal of an amino-protecting group from protected amino compound (17) for obtaining the desired compound (1) may be conducted in the same manner as in conventional methods for removing an amino-protecting group. For example, a t-butoxycarbonyl group can be removed by treating with an acid, such as trifluoroacetic acid, which is used in an amount of from 1 to 100 equivalents per equivalent of protected amino compound (17) in a reaction solvent, such as methanol, which is used in an amount which is 5 to 50 times the weight of protected amino compound (17), to thereby obtain the desired compound (1) having a vinyl group as R of formula (1). The reaction may be conducted at a temperature of from −20° C. to 100° C. for a period of from 0.5 hour to 30 hours.

The progress of each of the above-mentioned reactions can be traced by, for example, thin-layer chromatography (TLC), high performance liquid chromatography (HPLC) and the like. Therefore, the reaction can be terminated upon confirming that the amount of a reaction product has reached a maximum value, wherein the confirmation can be done by checking the concentration of a spot on a chromatograph.

The intermediate product obtained in each of the above-mentioned steps (which intermediate products are also novel compounds) is not usually isolated but used in situ in the subsequent reaction. However, if desired, each of these intermediate products may be isolated and purified prior to the subsequent reaction. Such treatments, namely, isolation and purification of the desired compound (1) and, if desired, those treatments of an intermediate product obtained in each of the steps, can be performed by conventional methods for isolating and purifying organic compounds wherein, for example, extraction, washing, concentrating, crystallization and chromatography are appropriately combined.

A pharmaceutically acceptable acid addition salt of the thus obtained compound (1) can be obtained by appropriate combination of conventional methods. For example, a method for obtaining a hydrochloride of compound (1) comprises dissolving compound (1) in a hydrophobic organic solvent, such as chloroform, to thereby obtain a solution, adding to the obtained solution an aqueous alkali solution, such as aqueous sodium hydroxide solution, to thereby obtain an aqueous layer and an organic layer, removing the aqueous layer to thereby obtain the organic layer, subjecting to the organic layer to distillation to thereby remove the solvent and obtain a residue, dissolving the residue in a hydrophilic organic solvent, such as methanol or ethanol, to thereby obtain a solution, applying the solution to an anion exchange resin equilibrated with hydrochloric acid, and eluting the desired compound (1) with the above-mentioned hydrophilic organic solvent.

For easy understanding of the steps of a process for producing the compound of the present invention represented by formula (1), a flow chart illustrating the steps is provided below.

Flow chart of the process for the production of compound (1)

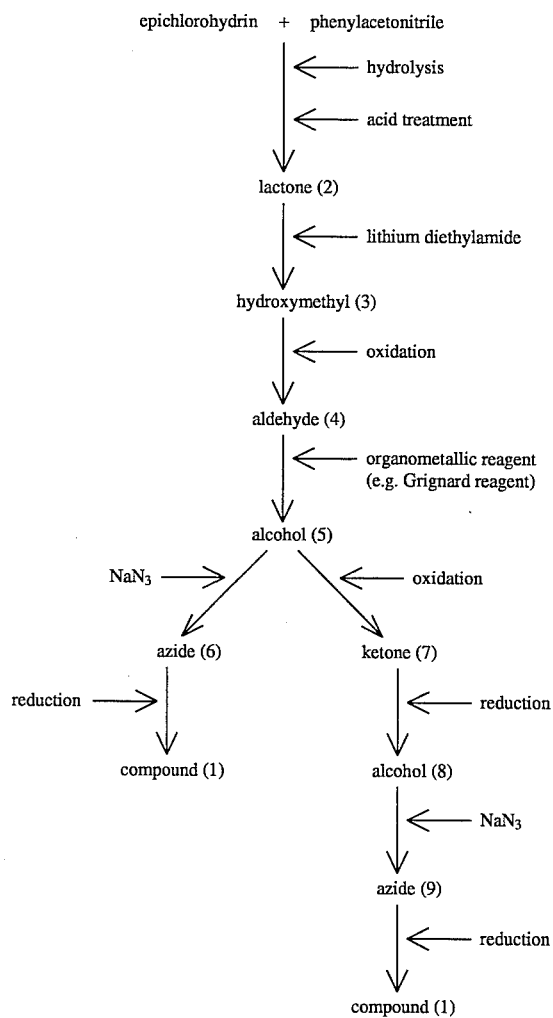

Compound (1) of the present invention, a racemic modification thereof, or a pharmaceutically acceptable acid addition salt of compound (1) or racemic modification thereof (hereinafter, referred to simply as "the compound of the present invention") can be administered alone, or in the from of a mixture with a pharmaceutically acceptable carrier, diluent or excipient. The proportions of components (including the compound of the present invention) in such a mixture can be appropriately selected depending on various factors, such as the manner of administration and the program of administration.

The compound of the present invention can be combined with other drugs, depending on the condition of the patient.

The compound of the present invention can be administered to a patient orally in the form of, for example, a tablet, capsule, powder, granule, liquid or elixir, or parenterally in the form of, for example, an injection, suppository, ointment or nasal drops.

Examples of solid carriers to be used in the oral administration include oligosaccharides, such as lactose, refined sugar and mannitol; excipients, such as starches (corn starch, potato starch and the like), crystalline cellulose, calcium phosphate and synthetic aluminum silicate; sodium salts or calcium salts, such as those of carboxymethyl cellulose; salts of fatty acid, such as magnesium stearate; talc; synthetic starches, such as hydroxypropylmethyl cellulose and methyl cellulose; gelatin, agar, gum and sodium alginate; and polyethylene glycol.

When the compound of the present invention is administered in the form of a capsule, tablet, granule or powder, the pharmaceutical composition is prepared so that it contains an isoquinoline sulfonamide derivative as an active component in an amount of from 1% to 80% by weight, preferably from 1% to 60% by weight.

When the compound of the present invention is orally administered in the form of a liquid, it is preferred that a solution or syrup containing the active component in an amount of 0.01% to 20% by weight be used. In this case, it is preferred that a flavoring agent, a sweetening agent and the like, in addition to water and ethanol, be added as a carrier.

When the compound of the present invention is parenterally administered by way of an intramuscular injection, an intravenous injection or a hypodermic injection, the compound of the present invention as an active component is used in the form of a sterilized solution to which another solute such as sodium chloride or glucose is added so that the solution becomes isotonic.

Examples of suitable solvents to be used in the injection include sterilized water, a solution of lidocaine hydrochloride (for intramuscular injection), physiological saline, glucose, a liquid for intravenous injection and a solution of electrolyte (for intravenous injection). It is preferred that the solvent to be used in the injection contain the compound of the present invention as an active component in an amount of from 0.01% to 20% by weight, preferably from 0.1% to 10% by weight.

When the compound of the present invention is administered in the form of a suppository or an ointment (endermic liniment), it is preferred that a pharmaceutical composition be prepared so that it contains the compound of the present invention as an active component in an amount of from 1% to 80% by weight. Examples of carriers to be used in the above-mentioned pharmaceutical composition include animal and vegetable oils such as petrolatum, paraffin, beeswax, lanolin and theobroma oil; synthetic oils such as macrogol and witepsol; an emulsifier; a preservative; and a sorbefacient.

When the compound of the present invention is transnasally administered, the active component can be formulated not only with the above-mentioned carriers to be used in a liquid, but also with an emulsifier, a sorbefacient and the like.

The dose of the compound of the present invention is varied depending on various factors, such as age, condition and weight of the patient, and symptom of the disease. When another treatment is simultaneously conducted, factors to be considered also include the type, frequency and desirable effect of the other treatment. However, the dose may generally be 0.01 to 60 mg/kg (weight of the patient) per day. Especially in the case of oral administration, it is preferred that the dose be 0.02 to 60 mg/kg (weight of the patient) per day, and in the case of parenteral administration, it is preferred that the dose be 0.01 to 20 mg/kg (weight of the patient) per day. The compound of the present invention may be administered once a day or several times a day.

The antagonistic activity, which compound (1) of the present invention or a pharmaceutically accepted acid addition salt thereof exhibits with respect to NMDA receptor, is described below.

In order to evaluate the capability of the compound of the present invention to inhibit $^3$H-MK801 from binding to NMDA receptor present on the membranes taken from rat cerebral cortices, the following tests were conducted with respect to compounds which were synthesized in Examples below, and the results are shown in Table 1. In the following tests, the above-mentioned known compound (A) was used as a control.

(1) Preparation of rat cerebral cortex membrane fraction

Five male SD strain rats (200–300 g) were decapitated, and the brains were taken out therefrom quickly. The cerebral cortices of the brains were extirpated, while keeping the brains immersed in ice-cooled 0.32M sucrose. The total weight of the cerebral cortices was 4.0 g. 120 ml of a 10 mM aqueous solution of N-2-hydroxyethylpiperadine-N'-2-ethanesulfonic acid (HEPES) (pH 7.4) was added to the cerebral cortices. The resultant suspension was homogenized at 500 rpm and then, subjected to centrifugation at 48,000× g for 15 minutes (hereinafter, centrifugation was carried out under the same conditions unless specified otherwise), to thereby obtain a precipitate. The precipitate was resuspended in 20 ml of deionized distilled water. The resultant suspension was incubated at 37° C. for 20 minutes to decompose glutamic acid and glycine contained in the cerebral cortical membrane, and then subjected to centrifugation to thereby obtain a precipitate. The precipitate was resuspended in 20 ml of deionized distilled water, and the resultant suspension was incubated at 37° C. for 20 minutes, and then subjected to centrifugation to thereby obtain a precipitate. The precipitate was resuspended in 20 ml of a 10 mM solution of HEPES (pH 7.4) containing 1 mM ethylenediaminetetraacetic acid (EDTA). The resultant suspension was incubated at 37° C. for 20 minutes, and then subjected to centrifugation to thereby obtain a precipitate. The obtained precipitate was resuspended in 26 ml of 10 mM HEPES (pH 7.4). The resultant suspension was separated into fractions each having a volume of 2 ml and preserved at −80° C. as cerebral cortical membrane fractions.

(2) Method for the evaluation of the capability to inhibit $^3$H-MK801 binding to the cerebral cortical membranes 2 ml of the freeze-preserved rat cerebral cortical membrane fraction prepared in step (1) above was thawed immediately before the measurement, and diluted with 30 ml of 10 mM HEPES (pH 7.4). The resultant dilution was subjected to centrifugation to thereby obtain a precipitate. The precipitate was resuspended in 30 ml of 10 mM HEPES (pH 7.4) so as to wash the precipitate containing cerebral cortical membranes. The resultant suspension was subjected to centrifugation to thereby obtain a precipitate. The precipitate was washed two more times by the same method as described above. The washed precipitate was resuspended in 6 ml of 10 mM HEPES (pH 7.4) and the resultant suspension was used as a membrane fraction for the measurement of the capability of $^3$H-MK801 to bind to the membranes.

To 0.1 ml of the above-mentioned membrane fraction were added the specimen (that is, the compound of the present invention), $^3$H-MK801 {common name: Dizocilpine, (5R, 10S)-(+)-5-methyl-10,11-dihydro-5H-dibenzo [a, d] cycloheptane-5,10-imine} [manufactured and sold by New England Nuclear Co., Ltd. U.S.A.; specific activity 24 Ci (888 GBq)/mM], glutamic acid and glycine, and was further added 10 mM HEPES (pH 7.4) so that the concentrations of the specimen, $^3$H-MK801, glutamic acid and glycine in the resultant solution having a volume of 1 ml became $10^{-6}$M, 4 nM, $10^{-5}$M and $10^{-5}$M, respectively. The solution was incubated for 60 minutes at 25° C. and then, incubation was terminated by rapid filtration through Whatman GF/G glass fiber filters (manufactured and sold by Whatman International Ltd., England). Subsequently, the filters were individually washed with 5 ml of 10 mM HEPES (pH 7.4) two times and then placed in a vial and dried. 5 ml of a liquid scintillator (containing toluene as a solvent) was added to each of the dried filters, and the radioactivity of each filter was measured to thereby quantitatively determine $^3$H-MK801 bound to NMDA receptor present on the cerebral cortical membranes. Specifically, a radioactivity value obtained by subtracting a radioactivity value as measured in the presence of 10 μM of phencyclidine (PCP) from the radioactivity value as measured in the absence of PCP, was used for calculating the amount of $^3$H-MK801 specifically bound to NMDA receptor. With respect to compound (A), which is a known compound, the inhibition ratio (%) for the binding of $^3$H-MK801 was measured and taken as 10%.

(3) Results

Capabilities of compound (1) of the present invention and pharmaceutically acceptable acid addition salts thereof to inhibit $^3$H-MK801 from binding to NMDA receptor present on the rat cerebral cortical membrane were determined in accordance with the above-described method. Results are shown in Table 1 below.

TABLE 1

| Specimen | | Inhibition ratio for the |
| --- | --- | --- |
| Compound | Amount | binding of $^3$H-MK801 (%) |
| A | $10^{-6}$ M | 10 |
| 7a | $10^{-6}$ M | 71 |
| 7b | $10^{-6}$ M | 75 |
| 31a | $10^{-6}$ M | 64 |
| 31b | $10^{-6}$ M | 67 |
| 7f | $10^{-6}$ M | 81 |

The above results indicate that the hydrochloride of compound (A) of the present invention exhibits remarkably high antagonistic activity with respect to NMDA receptor, as compared to known compound (A).

Therefore, compound (1) of the present invention, a racemic modification thereof, and a pharmaceutically acceptable acid addition salt of compound (1) or racemic modification thereof have remarkably high antagonistic activity with respect to NMDA receptor, as compared to known compounds having antagonistic activity with respect to NMDA receptor, and is useful as a preventive agent for cerebral infarction and a protective agent against ischemic diseases.

BEST MODE FOR CARRYING OUT THE INVENTION

Hereinbelow, the present invention will be described in more detail with reference to the following Reference Examples and Examples, but they should not be construed as limiting the scope of the present invention.

Reference Example 1 (production of a lactone from (R)-(−)-epichlorohydrin as a starting material), Reference Example 2 (production of a hydroxymethyl from the lactone), Reference Example 3 (production of an aldehyde from the hydroxymethyl), Reference Example 4 (production of an alcohol from the aldehyde), Reference Example 5 (production of an azide from the alcohol), Example 1 [production of compounds of the present invention (compounds 6a and 6b) from the azide] and Example 2 [production of acid addition salts of the present invention (compounds 7a and 7b) from compounds 6a and 6b, respectively] are shown below.

REFERENCE EXAMPLE 1

Production of (1S, 2R)-1-phenyl-2-hydroxymethylcyclopropane carboxylic anhydride (compound 1)

8.58 g (0.22 mmol) of sodium amide was suspended in 40 ml of anhydrous benzene. To the resultant suspension was dropwise added a solution of 11.5 ml (0.10 mol) of phenylacetonitrile in 20 ml of anhydrous benzene in a stream of argon gas at 0° C. After completion of the addition, the resultant mixture was stirred at room temperature for 3 hours to effect a reaction. To the resultant reaction mixture was dropwise added a solution of 6.8 ml (0.087 mol) of (R)-(−)-epichlorohydrin in 20 ml of anhydrous benzene while cooling with ice. After completion of the addition, the resultant mixture was stirred at room temperature for 2 hours to effect a reaction. After completion of the reaction, the resultant reaction mixture was subjected to distillation under reduced pressure to thereby remove the solvent and obtain a residue. 20 ml of ethanol and 10 ml of an aqueous 1N-KOH solution were added to the obtained residue, and the resultant mixture was refluxed for 15 hours to effect a reaction. After completion of the reaction, 12N hydrochloric acid was added to the mixture which cooling with ice to thereby acidify the mixture. The acidified mixture was concentrated under reduced pressure to thereby obtain a residue. A saturated aqueous sodium hydrogencarbonate solution was added to the obtained residue, and ethyl acetate was further added for extraction to obtain an organic layer. The organic layer was separated, washed with saturated saline, dried over anhydrous sodium sulfate, and subjected to distillation under reduced pressure to thereby remove the solvent and obtain a residue. The obtained residue was purified by silica gel column chromatography (the composition of the developing solvent was; ethyl acetate:hexane=1:3). As a result, 10.1 g (0.058 mol) of compound 1 (yield: 58%) was obtained as a yellow oily product.

REFERENCE EXAMPLE 2

Production of (1S, 2R)-1-phenyl-2-hydroxymethyl-cyclopropane N,N-diethylcarboxamide (compound 2)

1.7 ml (16 mmol) of diethylamine was dissolved in 20 ml of anhydrous tetrahydrofuran. To the resultant solution was dropwise added 11 ml (16 mmol) of a 1.64M hexane solution of butyllithium in a stream of argon gas at 0° C. to thereby obtain a solution containing lithium diethylamine. To the obtained solution containing lithium diethylamine was dropwise added a solution of 1.7 g (10 mmol) of compound 1 obtained in Reference Example 1 in 20 ml of anhydrous tetrahydrofuran in a stream of argon gas at −78° C. After completion of the addition; the resultant mixture was stirred at −78° C. for 2 hours to effect a reaction. To the obtained mixture was added a saturated aqueous ammonium chloride solution to thereby terminate the reaction and then, the resultant mixture was subjected to distillation under reduced pressure to thereby remove the solvent and obtain a residue. Water was added to the obtained residue, and ethyl acetate was further added for extraction to obtain an organic layer. The organic layer was separated, washed with saturated saline, dried over anhydrous sodium sulfate, and concentrated under reduced pressure to thereby obtain a residue. The obtained residue was purified by silica gel column chromatography (the composition of the developing solvent was; ethyl acetate:hexane=1:1). As a result, 2.1 g (8.7 mmol) of compound 2 (yield: 87%) was obtained as a yellow oily product.

REFERENCE EXAMPLE 3

Production of (1S, 2R)-1-phenyl-2-formylcyclopropane N,N-diethylcarboxamide (compound 3)

0.55 ml (6.40 mmol) of oxalylchloride was dissolved in 4 ml of anhydrous dichloromethane. To the resultant solution was dropwise added a solution of 0.91 ml (12.8 mmol) of dimethylsulfoxide in 4 ml of anhydrous dichloromethane in a stream of argon gas at −78° C., and the resultant mixture was stirred for 30 minutes to effect a reaction. To the resultant reaction mixture was dropwise added a solution of 805 mg (3.26 mmol) of compound 2 obtained in Reference Example 2 in 4 ml of anhydrous dichloromethane at −78° C. The resultant mixture was stirred for 2 hours to effect a reaction. To the resultant reaction mixture was added 1.9 ml (25.6 mmol) of triethylamine, and the mixture was stirred for 1 hour. To the obtained mixture was added a saturated aqueous ammonium chloride solution to thereby terminate the reaction and then, chloroform was added to the resultant mixture for extraction to obtain an organic layer. The organic layer was separated, washed with saturated saline, dried over anhydrous sodium sulfate, and concentrated under reduced pressure to thereby obtain a residue. The obtained residue was purified by silica gel column chromatography (the composition of the developing solvent was; ethyl acetate:hexane=2:1). As a result, 791 mg (3.22 mmol) of compound 3 (yield: 99%) was obtained as a white crystalline product.

REFERENCE EXAMPLE 4

Production of (1S, 2R, 2'S)-1-phenyl-2-(1-hydroxyethyl)-cyclopropane N,N-diethylcarboxamide (compound 4a) and (1S, 2R, 2'S)-1-phenyl-2-(1-hydroxypropyl)-cyclopropane N,N-diethylcarboxamide (compound 4b)

Compound 3 (6.5 mmol) obtained in Reference Example 3 was dissolved in 40 ml of anhydrous tetrahydrofuran. To the resultant solution were individually added Grignard reagents (13 mmol of CH$_3$MgBr and 13 mmol of C$_2$H$_5$MgBr) in a stream of argon gas at −20° C., and each of the resultant mixtures was stirred for 2 hours to effect a reaction. To each of the obtained mixtures was added a saturated aqueous ammonium chloride solution to thereby terminate the reaction and then, the resultant mixture was subjected to distillation under reduced pressure to thereby remove the solvent and obtain a residue. Water was added to each of the obtained residues, and ethyl acetate was further added for extraction to obtain an organic layer. Each of the organic layers was separated, washed with saturated saline, dried over anhydrous sodium sulfate, and concentrated under reduced pressure to thereby obtain a residue. Each of the obtained residues was purified by silica gel column chromatography (the composition of the developing solvent was; ethyl acetate:hexane=1:2). As a result compound 4a (6.0 mmol, yield: 92%) was obtained when $CH_3MgBr$ was used as Grignard reagent, and compound 4b (6.4 mmol, yield: 98%) was obtained when $C_2H_5MgBr$ was used as Grignard reagent.

REFERENCE EXAMPLE 5

Production of (1S, 2R, 2,S)-1-phenyl-2-(1-azidoethyl)-N,N-diethylcyclopropane carboxamide (compound 5a) and (1S, 2R, 2,S)-1-phenyl-2-(1-azidopropyl)-N,N-diethylcyclopropane carboxamide (compound 5b)

Compounds 4a and 4b (each, 3.8 mmol) obtained in Reference Example 4 were individually dissolved in 10 ml of dimethylformamide. To each of the resultant solutions were added sodium azide (72 mmol), triphenylphosphine (11 mmol) and carbon tetrabromide (11 mmol) in this order while cooling with ice. Then, the temperature of each of the resultant mixtures was allowed to return to room temperature, and each of the mixtures was stirred for 3 hours to effect a reaction. After completion of the reaction, each of the resultant reaction mixtures was subjected to distillation under reduced pressure to thereby remove the solvent and obtain a residue. Water was added to each of the obtained residues, and ethyl acetate was further added for extraction to obtain an organic layer. Each of the organic layers was separated, washed with saturated saline, dried over anhydrous sodium sulfate, and concentrated under reduced pressure to thereby obtain a residue. Each of the obtained residues was purified by silica gel column chromatography (the composition of the developing solvent for the residue obtained from compound 4a was; ethyl acetate:hexane=1:5, and the composition of the developing solvent for the residue obtained from compound 4b was; ethyl acetate:hexane=1:9). As a result, compound 5a (2.5 mmol, yield: 66%) was obtained from compound 4a and compound 5b (yield: 62%) was obtained from compound 4b.

EXAMPLE 1

Production of (1S, 2R, 2'S)-1-phenyl-2-(1-aminoethyl)-cyclopropane N,N-diethylcarboxamide (compound 6a) and (1S, 2R, 2'S)-1-phenyl-2-(1-aminopropyl)-cyclopropane N,N-diethylcarboxamide (compound 6b)

Compounds 5a and 5b (each, 2.1 mmol) obtained in Reference Example 5 were individually dissolved in 10 ml of methanol. To each of the resultant solutions was added 44 mg of 10% Pd-carbon, and each of the resultant mixtures was stirred at room temperature for 1 hour in a hydrogen gas atmosphere. Each of the resultant mixtures was subjected to filtration by means of Celite, and each of the resultant filtrates was concentrated under reduced pressure to thereby obtain a residue. Each of the residues was purified by silica gel column chromatography (the composition of the developing solvent for the residue obtained from compound 5a was; chloroform:methanol:aqueous ammonia=10:1:0.2, and the composition of the developing solvent for the residue obtained from compound 5b was; chloroform:methanol:aqueous ammonia:water=65:25:1:2). As a result, compound 6a (1.7 mmol, yield: 82%) was obtained from compound 5a and compound 6b (yield: 95%) was obtained from compound 5b.

EXAMPLE 2

Production of (1S, 2R, 2'S)-1-phenyl-2-(1-aminoethyl)-cyclopropane N,N-diethylcarboxamide hydrochloride (compound 7a) and (1S, 2R, 2'S)-1-phenyl-2-(1-aminopropyl)-cyclopropane N,N-diethylcarboxamide hydrochloride (compound 7b)

Diaion WA-30 (ion exchange resin manufactured and sold by Mitsubishi Chemical Industries, Ltd., Japan) was treated with an aqueous 1N-NaOH solution and washed with distilled water to thereby render neutral the resin. The resin was further treated with 1N hydrochloric acid and washed with distilled water to thereby render neutral the resin. The resultant resin was used in the purification of compounds described below.

Compounds 6a and 6b (each, 1.7 mmol) obtained in Example 1 were individually dissolved in chloroform. To each of the resultant solutions was added an aqueous 1N-NaOH solution to thereby obtain an organic layer. Each of the organic layers was separated, washed with saturated saline, dried over anhydrous sodium sulfate, and subjected to distillation under reduced pressure to thereby remove the solvent and obtain a residue. Each of the obtained residues was individually dissolved in methanol, and the resultant solution was applied to a column packed with the above-prepared ion exchange resin and eluted with methanol. Each of the eluates was concentrated under reduced pressure to thereby obtain crystals. The crystals obtained from the respective eluates were washed with diethyl ether. As a result, compound 7a (1.1 mmol, yield: 65%) was obtained from compound 6a, and compound 7b (yield: 91%) was obtained from compound 6b, both as a white powdery product.

The process for the production of compounds of the present invention (compounds 6a and 6b) and acid addition salts thereof of the present invention (compounds 7a and 7b) from the (R)-(–)-epichlorohydrin as a starting material, which process is described in the above-mentioned Reference Examples 1 to 5 and Examples 1 and 2, is illustrated in the following flow sheet.

Flow sheet of the reactions conducted in Reference Examples 1 to 5 and Examples 1 and 2

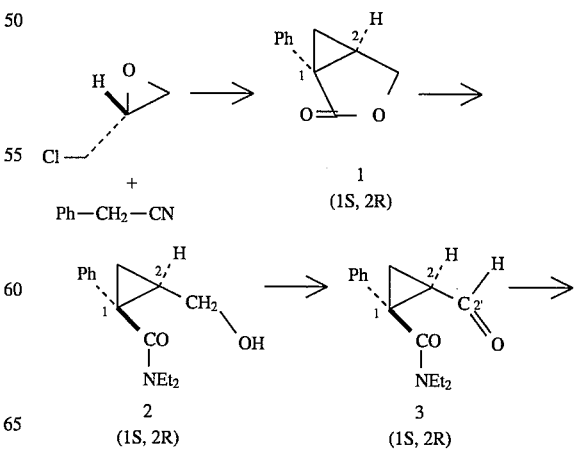

-continued
Flow sheet of the reactions conducted in
Reference Examples 1 to 5 and Examples 1 and 2

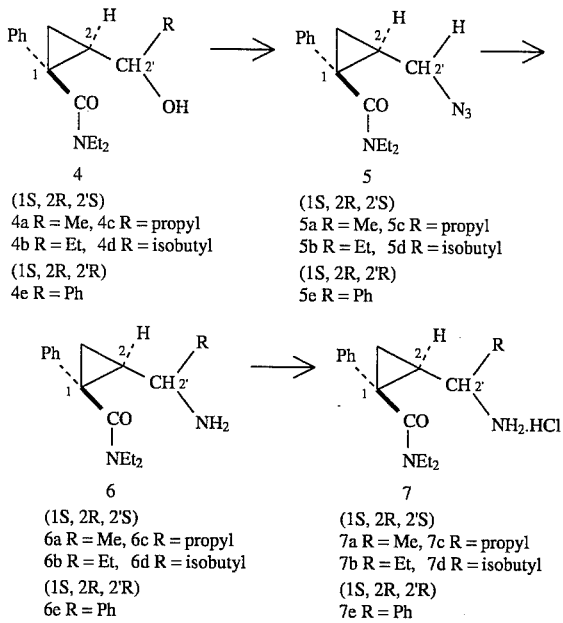

4
(1S, 2R, 2'S)
4a R = Me, 4c R = propyl
4b R = Et, 4d R = isobutyl
(1S, 2R, 2'R)
4e R = Ph 5
(1S, 2R, 2'S)
5a R = Me, 5c R = propyl
5b R = Et, 5d R = isobutyl
(1S, 2R, 2'R)
5e R = Ph 6
(1S, 2R, 2'S)
6a R = Me, 6c R = propyl
6b R = Et, 6d R = isobutyl
(1S, 2R, 2'R)
6e R = Ph 7
(1S, 2R, 2'S)
7a R = Me, 7c R = propyl
7b R = Et, 7d R = isobutyl
(1S, 2R, 2'R)
7e R = Ph The results of the nuclear magnetic resonance spectroscopic analysis of the products obtained in Reference Examples 1 to 5 and Examples 1 and 2 are shown in Table 2 below.

Reference Example 6 [production of ketones from the alcohols (compounds 4a and 4b) obtained in Reference Example 4], Reference Example 7 (production of alcohols from the ketones), Reference Example 8 (production of azides from the alcohols), Example 3 [production of compounds of the present invention (compounds 11a and 11b) from the azides] and Example 4 [production of acid addition salts of the present invention (compounds 12a and 12b) from compounds 11a and 11b, respectively] are shown below.

EXAMPLE 6

Production of (1S, 2R)-1-phenyl-2-(1-oxoethyl)-cyclopropane N,N-diethylcarboxamide (compound 8a) and (1S, 2R)-1-phenyl-2-(1-oxopropyl)-cyclopropane N,N-diethylcarboxamide (compound 8d)

Compounds 4a and 4b (each, 5.4 mmol) obtained in Reference Example 4 were individually dissolved in 20 ml of dichloromethane. To each of the resultant solutions were added 19 mmol of pyridinium dichromate and 7 g of powder of molecular sieve 4A (manufactured and sold by Wako Pure Chemical industries, Ltd., Japan), and each of the resultant mixtures was stirred at room temperature overnight. Each of the resultant mixtures was subjected to filtration by means of Celite, and each of the resultant filtrates was concentrated under reduced pressure to thereby obtain a residue. Each of the obtained residues was purified by silica gel column chromatography (the composition of the developing solvent was; ethyl acetate:hexane=1:2). As a result, compound 8a (5.2 mmol, yield: 96%) was obtained from compound 4a and compound 8b (yield: 87%) was obtained from compound 4b.

REFERENCE EXAMPLE 7

Production of (1S, 2R, 2'R)-1-phenyl-2-(1-hydroxyethyl)-N,N-diethylcyclopropane carboxamide (compound 9a) and (1S, 2R, 2'R)-1-phenyl-2-(1-hydroxypropyl)-N,N-diethylcyclopropane carboxamide (compound 9b)

Compounds 8a and 8b (each, 3.73 mmol) obtained in Reference Example 6 were individually dissolved in 20 ml of anhydrous tetrahydrofuran. To each of the resultant solutions was added 7.46 mmol of a 0.93M hexane solution of diisobutylaluminum hydride in a stream of argon gas at −78° C., and each of the resultant mixtures was stirred at −78° C. for 1 hour to effect a reaction. To each of the obtained mixtures was added 1N hydrochloric acid to thereby terminate the reaction and then, each of the resultant mixtures was subjected to distillation under reduced pressure to thereby remove the solvent and obtain a residue. Water was added to each of the obtained residues, and ethyl acetate was further added for extraction to obtain an organic layer. Each of the organic layers was separated, washed with saturated saline, dried over anhydrous sodium sulfate, and concentrated under reduced pressure to thereby obtain a residue. Each of the obtained residues was purified by silica gel column chromatography (the composition of the developing solvent for the residue obtained from compound 8a was; ethyl acetate:hexane=1:1, and the composition of the developing solvent for the residue obtained from compound 8b was; ethyl acetate:hexane=1:2). As a result, compound 9a (3.66 mmol, yield: 96%) was obtained from compound 8a, and compound 9b (yield: 100%) was obtained from compound 8b.

REFERENCE EXAMPLE 8

Production of (1S, 2R, 2'R)-1-phenyl-2-(1-azidoethyl)-N,N-diethylcyclopropane carboxamide (compound 10a) and (1S, 2R, 2'R)-1-phenyl-2-(1-azidopropyl)-N,N-diethylcyclopropane carboxamide (compound 10b)

Compounds 9a and 9b (each, 3.8 mmol) obtained in Reference Example 7 were individually dissolved in 10 ml of dimethylformamide. To each of the resultant solutions were added sodium azide (72 mmol), triphenylphosphine (11 mmol) and carbon tetrabromide (11 mmol) in this order while cooling with ice. Then, the temperature of each of the resultant mixtures was allowed to return to room temperature, and each of the mixtures was stirred for 3 hours to effect a reaction. After completion of the reaction, each of the resultant reaction mixtures was subjected to distillation under reduced pressure to thereby remove the solvent and obtain a residue. Water was added to each of the obtained residues, and ethyl acetate was further added for extraction to obtain an organic layer. Each of the organic layers was separated, washed with saturated saline, dried over anhydrous sodium sulfate, and concentrated under reduced pressure to thereby obtain a residue. Each of the obtained residues was purified by silica gel column chromatography (the composition of the developing solvent for the residue obtained from compound 9a was; ethyl acetate:hexane=1:5, and the composition of the developing solvent for the residue obtained from compound 9b was; ethyl acetate:hexane=1:9). As a result, compound 10a (yield: 84%) was obtained from compound 9a and compound 10b (yield: 89%) was obtained from compound 9b.

EXAMPLE 3

Production of (1S, 2R, 2'R)-1-phenyl-2-(1-aminoethyl)-cyclopropane N,N-diethylcarboxamide (compound 11a) and (1S, 2R, 2'R)-1-phenyl-2-(1-aminopropyl)-cyclopropane N,N-diethylcarboxamide (compound 11b)

Compounds 10a and 10b (each, 2.1 mmol) obtained in Reference Example 8 were individually dissolved in 10 ml of methanol. To each of the resultant solutions was added 44 mg of 10% Pd-carbon and each of the resultant mixtures was stirred for 1 hour at room temperature in a hydrogen gas atmosphere. Each of the resultant mixtures was subjected to filtration by means of Celite, and each of the resultant filtrates was concentrated under reduced pressure to thereby obtain a residue. Each of the residues was purified by silica gel column chromatography (the composition of the developing solvent for the residue obtained from compound 10a was; chloroform:methanol:aqueous ammonia=80:20:0.5, and the composition of the developing solvent for the residue obtained from compound 10b was; chloroform: methanol: aqueous ammonia=90:20:0.5). As a result compound 11a (yield: 90%) was obtained from compound 10a and compound 11b (yield: 99%) was obtained from compound 10b.

EXAMPLE 4

Production of (1S, 2R, 2'R)-1-phenyl-2-(1-aminoethyl)-cyclopropane N,N-diethylcarboxamide hydrochloride (compound 12a) and (1S, 2R, 2'R)-1-phenyl-2-(1-aminopropyl)-cyclopropane N,N-diethylcarboxamide hydrochloride (compound 12b)

Compounds 11a and 11b (each, 1.7 mmol) obtained in Example 3 were individually treated in the same manner as in Example 2. As a result, compounds 12a (yield: 81%) and compound 12b (yield: 84%) were obtained, both as a white powdery product.

The process for the production of compounds of the present invention (compounds 11a and 11b) and acid addition salts thereof of the present invention (compounds 12a and 12b) from the intermediate products (alcohol; compounds 4a and 4b) obtained in Reference Example 4, which process is described in the above-mentioned Reference Examples 6 to 8 and Examples 3 and 4, is illustrated in the following flow sheet.

Flow sheet of the reactions conducted in
Reference Examples 6 to 8 and Examples 3 and 4

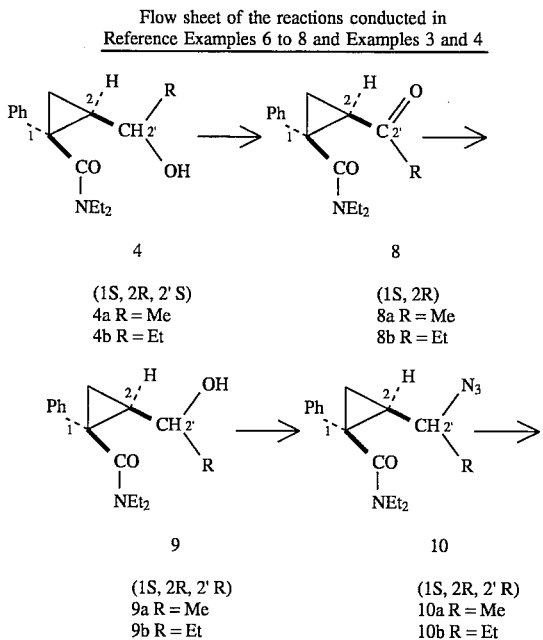

-continued
Flow sheet of the reactions conducted in
Reference Examples 6 to 8 and Examples 3 and 4

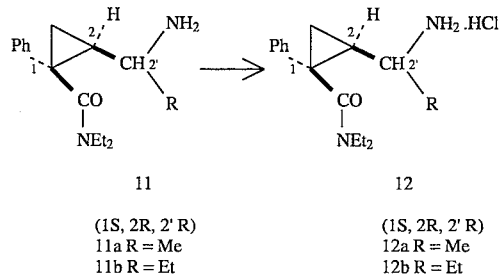

The results of the nuclear magnetic resonance spectroscopic analysis of the products obtained in Reference Examples 6 to 8 and Examples 3 to 4 were shown in Table 2 below.

Reference Example 9 (production of a lactone from (S)-(+)-epichlorohydrin as a starting material), Reference Example 10 (production of a hydroxy methyl from the lactone), Reference Example 11 (production of an aldehyde from the hydroxymethyl), Reference Example 12 (production of an alcohol from the aldehyde), Reference Example 13 (production of an azide from the alcohol), Example 5 [production of compounds of the present invention (compounds 18a and 18b) from the azide], and Example 6 [production of acid addition salts of the present invention (compounds 19a and 19b) from compounds 18a and 18b, respectively] are shown below.

REFERENCE EXAMPLE 9

Production of (1R, 2S)-1-phenyl-2-hydroxymethyl cyclopropane carboxylic anhydride (compound 13)

8.58 g (0.22 mol) of sodium amide was suspended in 40 ml of anhydrous benzen. To the resultant suspension was dropwise added a solution of 11.5 ml (0.10 mol) of phenylacetonitrile in 20 ml of anhydrous benzen in a stream of argon gas at 0° C. After the addition, the resultant mixture was stirred at room temperature for 3 hours to effect a reaction. To the resultant mixture was dropwise added a solution of 6.8 ml (0.087 mol) of (S)-(+)-epichlorohydrin in 20 ml of anhydrous benzen while cooling with ice. After the addition, the resultant mixture was stirred at room temperature for 2 hours to effect a reaction. After completion of the reaction, the resultant mixture was subjected to distillation under reduced pressure to thereby remove the solvent and obtain a residue. To the obtained residue were added 20 ml of ethanol and 10 ml of an aqueous 1N-KOH solution. The resultant mixture was refluxed for 15 hours to effect a reaction. After completion of the reaction, 12N hydrochloric acid was added to the resultant reaction mixture to thereby acidify the mixture, and the acidified mixture was concentrated under reduced pressure to thereby obtain a residue. A saturated aqueous sodium hydrogencarbonate solution was added to the obtained residue, and ethyl acetate was further added for extraction to obtain an organic layer. The organic layer was separated, washed with saturated saline, dried over anhydrous sodium sulfate, and subjected to distillation under reduced pressure to thereby remove the solvent and obtain a residue. The residue was purified by silica gel column chromatography (the composition of the developing solvent was; ethyl acetate:hexane=1:3). As a result, compound 13 (10.0 g) was obtained as an orange oily product.

REFERENCE EXAMPLE 10

Production of (1R, 2S)-1-phenyl-2-hydroxymethyl cyclopropane N,N-diethylcarboxamide (compound 14)

1.7 ml (16 mmol) of diethylamine was dissolved in 20 ml anhydrous tetrahydrofuran. To the resultant solution was dropwise added 11 ml (16 mmol) of a 1.64M hexane solution of butyllithium in a stream of argon gas at 0° C., to thereby obtain lithium diethylamine. To the resultant mixture was dropwise added a solution of 1.7 g (10 mmol) of compound 13 obtained in Reference Example 9 in 20 ml of anhydrous tetrahydrofuran in a stream of argon gas at −78° C. After the addition, the resultant mixture was stirred at −78° C. for 2 hours to effect a reaction. To the resultant mixture was added a saturated aqueous ammonium chloride solution to thereby terminate the reaction and then, the resultant mixture was subjected to distillation under reduced pressure to thereby remove the solvent and obtain a residue. Water was added to the obtained residue, and ethyl acetate was further added for extraction to obtain an organic layer. The organic layer was separated, washed with saturated saline, dried over anhydrous sodium sulfate, and concentrated under reduced pressure to thereby obtain a residue. The obtained residue was purified by silica gel column chromatography (the composition of the developing solvent was; ethyl acetate:hexane=1:1). As a result, compound 14 (2.0 g) was obtained as a yellow oily product.

REFERENCE EXAMPLE 11

(1R, 2S)-1-phenyl-2-formylcyclopropane N,N-diethylcarboxamide (compound 15)

0.55 ml (6.40 mmol) of oxalylchloride was dissolved in 4 ml of anhydrous dichloromethane. To the resultant solution was dropwise added a solution of 0.91 ml (12.8 mmol) of dimethylsulfoxide in 4 ml of anhydrous dichloromethane in a stream of argon gas at −78° C. The resultant mixture was stirred for 30 minutes and then, a solution of 805 mg (3.26 mmol) of compound 14 obtained in Reference Example 10 in 4 ml of anhydrous dichloromethane was dropwise added to the mixture at −78° C. The resultant mixture was stirred for 2 hours to effect a reaction. 1.9 ml (25.6 mmol) of triethylamine was added to the reaction mixture. The resultant mixture was stirred for 1 hour, and then, a saturated aqueous ammonium chloride solution was added to the mixture to thereby terminate the reaction. Chloroform was added to the mixture for extraction to obtain an organic layer. The organic layer was separated, washed with saturated saline, dried over anhydrous sodium sulfate, and concentrated under reduced pressure to thereby obtain a residue. The residue was purified by silica gel column chromatography (the composition of the developing solvent was; ethyl acetate:hexane=2:1). As a result, compound 15 (790 mg) was obtained as a white crystalline product.

REFERENCE EXAMPLE 12

Production of (1R, 2S, 2'R)-1-phenyl-2-(1-hydroxyethyl)-cyclopropane N,N-diethylcarboxamide (compound 16a) and (1R, 2S, 2'R)-1-phenyl-2-(1-hydroxypropyl)-cyclopropane N,N-diethylcarboxamide (compound 16b)

Compound 15 (6.5 mmol) obtained in Reference Example 11 was dissolved in 40 ml of anhydrous tetrahydrofuran. To the resultant solution were individually added Grignard reagents (13 mmol of $C_3H_7MgBr$ and 13 mmol of $C_2H_5MgBr$) in a stream of argon gas at −20° C., and each of the resultant mixtures was stirred for 2 hours to effect a reaction. To each of the obtained mixtures was added a saturated aqueous ammonium chloride solution to thereby terminate the reaction and then, the resultant mixture was subjected to distillation under reduced pressure to thereby remove the solvent and obtain a residue. Water was added to each of the obtained residues, and ethyl acetate was further added for extraction to obtain an organic layer. Each of the organic layers was separated, washed with saturated saline, dried over anhydrous sodium sulfate, and concentrated under reduced pressure to thereby obtain a residue. Each of the obtained residues was purified by silica gel column chromatography (the composition of the developing solvent was; ethyl acetate:hexane=1:2). As a result, compound 16a (yield: 91%) was obtained when $CH_3MgBr$ was used as Grignard reagent, and compound 16b (yield: 97%) was obtained when $C_2H_5MgBr$ was used as Grignard reagent.

REFERENCE EXAMPLE 13

Production of (1R, 2S, 2'R)-1-phenyl-2-(1-azidoethyl)-N,N-diethylcyclopropane carboxamide (compound 17a) and (1R, 2S, 2'R)-1-phenyl-2-(1-azidopropyl)-N,N-diethylcyclopropane carboxamide (compound 17b)

Compounds 16a and 16b (each, 3.8 mmol) obtained in Reference Example 12 were individually dissolved in 10 ml of dimethylformamide. To each of the resultant solutions was added sodium azide (72 mmol), triphenylphosphine (11 mmol) and carbon tetrabromide (11 mmol) in this order while cooling with ice. Then, the temperature of each of the resultant mixtures was allowed to return to room temperature, and each of the mixtures was stirred for 3 hours to effect a reaction. After completion of the reaction, each of the resultant reaction mixtures was subjected to distillation under reduced pressure to thereby remove the solvent and obtain a residue. Water was added to each of the obtained residues, and ethyl acetate was further added for extraction to obtain an organic layer. Each of the organic layers was separated, washed with saturated saline, dried over anhydrous sodium sulfate, and concentrated under reduced pressure to thereby obtain a residue. Each of the obtained residues was purified by silica gel column chromatography (the composition of the developing solvent for the residue obtained from compound 16a was; ethyl acetate:hexane= 1:5, and the composition of the developing solvent for the residue obtained from compound 16b was; ethyl acetate:hexane=1:9). As a result, compound 17a (yield: 65%) was obtained from compound 16a, and compound 17b (yield: 61%) was obtained from the compound 16b.

EXAMPLE 5

Production of (1R, 2S, 2'R)-1-phenyl-2-(1-aminoethyl)-cyclopropane N,N-diethylcarboxamide (compound 18a) and (1R, 2S, 2'R)-1-phenyl-2-(1-aminoypropyl)-cyclopropane N,N-diethylcarboxamide (compound 18b)

Compounds 17a and 17b (each, 2.1 mmol) obtained in Reference Example 13 were individually dissolved in 10 ml of methanol. To each of the resultant solutions was added 44 mg of 10% Pd-carbon, and each of the resultant mixtures was stirred at room temperature for 1 hour in a hydrogen gas atmosphere. Each of the resultant mixtures was subjected to filtration by means of Celite, and each of the resultant filtrates was concentrated under reduced pressure to thereby obtain a residue. Each of the residues was purified by silica gel column chromatography (the composition of the developing solvent for the residue obtained from compound 17a was; chloroform:methanol:aqueous ammonia=10:1:0.2, and the composition of the developing solvent for the residue obtained from compound 17b was; chloroform:methanol:aqueous ammonia:water=65:25:1:2). As a result, compound 18a (yield: 81%) was obtained from compound 17a and compound 18b (yield: 94%) was obtained from compound 17b.

EXAMPLE 6

Production of (1R, 2S, 2'R)-1-phenyl-2-(1-aminoethyl)-cyclopropane N,N-diethylcarboxamide hydrochloride (compound 19a) and (1R, 2S, 2'R)-1-phenyl-2-(1-aminoypropyl)-cyclopropane N,N-diethylcarboxamide hydrochloride (compound 19b)

Diaion WA-30 (ion exchange resin manufactured and sold by Mitsubishi Chemical Industries, Ltd., Japan) was treated with an aqueous 1N-NaOH solution and washed with distilled water to thereby render neutral the resin. The resin was further treated with 1N hydrochloric acid and washed with distilled water to thereby render neutral the resin. The resultant resin was used in the purification of compounds described below.

Compounds 18a and 18b (each, 1.7 mmol) obtained in Example 5 were individually dissolved in chloroform. To each of the resultant solutions was added an aqueous 1N-NaOH solution to thereby obtain an organic layer. Each of the organic layers was separated, washed with saturated saline, dried over anhydrous sodium sulfate, and subjected to distillation under reduced pressure to thereby remove the solvent and obtain a residue. Each of the obtained residues was individually dissolved in methanol, and the resultant solution was applied to a column packed with the above-prepared ion exchange resin and eluted-with methanol. Each of the eluates was concentrated under reduced pressure to thereby obtain crystals. The crystals obtained from the respective eluates were washed with diethyl ether. As a result, compound 19a (yield: 64%) was obtained from compound 18a and compound 19b (yield: 90%) was obtained from compound 18b, both as a white powdery product.

The process for the production of compounds of the present invention (compounds 18a and 18b) and acid addition salts thereof of the present invention (compounds 19a and 19b) from the (R)-(−)-epichlorohydrin as a starting material, which process is described in the above-mentioned Reference Examples 9 to 13 and Examples 5 and 6, is illustrated in the following flow sheet.

Flow sheet of the reactions conducted in
Reference Examples 9 to 13 and Examples 5 and 6

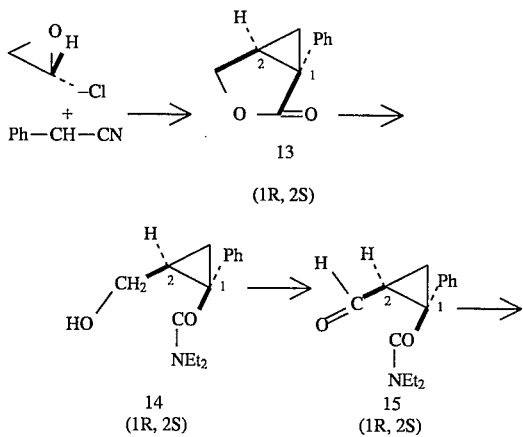

-continued
Flow sheet of the reactions conducted in
Reference Examples 9 to 13 and Examples 5 and 6

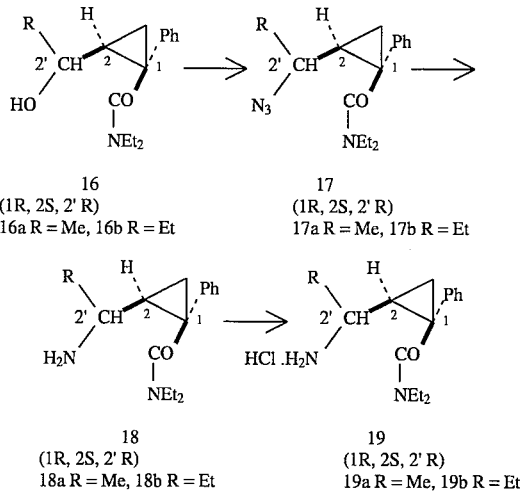

The results of the nuclear magnetic resonance spectroscopic analysis of the products obtained in Reference Examples 9 to 13 and Example 5 and 6 were, respectively, in agreement with the results, shown in Table 2 below, of the nuclear magnetic resonance spectroscopic analysis of products obtained in Reference Examples 1 to 5 and Examples 1 and 2.

Reference Example 14 [production of ketones from the alcohols (compounds 16a and 16b) obtained in Reference Example 12], Reference Example 15 (production of alcohols from the ketones), Reference Example 16 (production of azides from the alcohols), Example 7 [production of compounds of the present invention (compounds 23a and 23b) from the azides] and Example 8 [production of acid addition salts of the present invention (compounds 24a and 24b) from compounds 23a and 23b, respectively] are shown below.

REFERENCE EXAMPLE 14

Production of (1R, 2S)-1-phenyl-2-(1-oxoethyl)-cyclopropane N,N-diethylcarboxamide (compound 20a) and (1R, 2S)-1-phenyl-2-(1-oxopropyl)-cyclopropane N,N-diethylcarboxamide (compound 20b)

Compounds 16a and 16b (each, 5.4 mmol each) obtained in Reference Example 12 were individually dissolved in 20 ml of dichloromethane. To each of the resultant solutions were added 19 mmol of pyridinium dichromate and 7 g of powder of molecular sieve 4A (manufactured and sold by Wako Pure Chemical Industries, Ltd., Japan) and each of the resultant mixtures was stirred at room temperature overnight. Each of the resultant mixtures was subjected to filtration by means of Celite, and each of the resultant filtrates was concentrated under reduced pressure to thereby obtain a residue. Each of the residues was purified by silica gel column chromatography (the composition of the developing solvent was; ethyl acetate:hexane=1:2). As a result, compound 20a (yield: 95%) was obtained from compound 16a, and compound 20b (yield: 86%) was obtained from compound 16b.

REFERENCE EXAMPLE 15

Production of (1R, 2S, 2'S)-1-phenyl-2-(1-hydroxyethyl)-N,N-diethylcyclopropane carboxamide (compound 21a) and (1R, 2S, 2'S)-1-phenyl-2-(1-hydroxypropyl)-N,N-diethylcyclopropane carboxamide (compound 21b)

Compounds 20a and 20b (each, 3.73 mmol) obtained in Reference Example 14 were individually dissolved in 20 ml of anhydrous tetrahydrofuran. To each of the resultant solutions was added a solution of 0.93M diisobutylaluminumhydride in hexane (7.46 mmol) in a stream of argon gas at −78° C. Each of the resultant mixtures was stirred at −78° C. for 1 hour to effect a reaction. 1N hydrochloric acid was added to each of the reaction mixtures to thereby terminate the reaction. The resultant mixture was subjected to distillation under reduced pressure to thereby remove the solvent and obtain a residue. Water was added to each of the obtained residues, and ethyl acetate was further added for extraction to thereby obtain an organic layer. Each of the organic layers was separated, washed with saturated saline, dried over anhydrous sodium sulfate, and concentrated under reduced pressure to thereby obtain a residue. Each of the obtained residues was purified by silica gel column chromatography (the composition of the developing solvent for the residue obtained from compound 20a was; ethyl acetate:hexane =1:1, and the composition of the developing solvent for the residue obtained from compound 20b was; ethyl acetate:hexane=1:2). As a result, compound 21a was obtained from compound 20a (yield: 95%), and compound 21b was obtained from compound 20b (yield: 99%).

REFERENCE EXAMPLE 16

Production of (1R, 2S, 2'S)-1-phenyl-2-(1-azidoethyl)-N,N-diethylcyclopropane carboxamide (compound 22a) and (1R, 2S, 2'S)-1-phenyl-2-(1-azidopropyl)-N,N-diethylcyclopropane carboxamide (compound 22b)

Compounds 21a and 21b (each, 3.8 mmol) obtained in Reference Example 15 were individually dissolved in 10 ml of dimethylformamide. To each of the resultant solutions were added sodium azide (72 mmol) triphenylphosphine (11 mmol) and carbon tetrabromide (11 mmol) in this order while cooling with ice. Then, the temperature of each of the resultant mixtures was allowed to return to room temperature, and each of the mixtures was stirred for 3 hours to effect a reaction. After completion of the reaction, each of the resultant reaction mixtures was subjected to distillation under reduced pressure to thereby remove the solvent and obtain a residue. Water was added to each of the obtained residues, and ethyl acetate was further added for extraction to obtain an organic layer. Each of the organic layers was separated, washed with saturated saline, dried over anhydrous sodium sulfate, and concentrated under reduced pressure to thereby obtain a residue. Each of the obtained residues was purified by silica gel column chromatography (the composition of the developing solvent for the residue obtained from compound 21a was; ethyl acetate:hexane= 1:5, and the composition of the developing solvent for the residue obtained from compound 21b was; ethyl acetate:hexane=1:9). As a result, compound 22a (yield: 83%) was obtained from compound 21a, and compound 22b (yield: 88%) was obtained from compound 21b.

EXAMPLE 7

Production of (1R, 2S, 2'S)-1-phenyl-2-(1-aminoethyl)-cyclopropane N,N-diethylcarboxamide (compound 23a) and (1R, 2S, 2'S)-1-phenyl-2-(1-aminopropyl)-cyclopropane N,N-diethylcarboxamide (compound 23b)

Compounds 22a and 22b (each, 2.1 mmol) obtained in Reference Example 16 were individually dissolved in 10 ml of methanol. To each of the resultant solutions was added 44 mg of 10% Pd-carbon and each of the resultant mixtures was stirred for 1 hour at room temperature in a hydrogen gas atmosphere. Each of the resultant mixtures was subjected to filtration by means of Celite, and each of the resultant filtrates was concentrated under reduced pressure to thereby obtain a residue. Each of the obtained residues was purified by silica gel column chromatography (the composition of the developing solvent for the residue obtained from compound 22a was; chloroform:methanol:aqueous ammonia= 80:20:0.5, and the composition of the developing solvent for the residue obtained from compound 22b was; chloroform:methanol:aqueous ammonia=90:20:0.5). As a result, compound 23a (yield: 89%) was obtained from compound 22a, and compound 23b (yield: 98%) was obtained from compound 22b.

EXAMPLE 8

Production of (1R, 2S, 2'S)-1-phenyl-2-(1-aminoethyl)-cyclopropane N,N-diethylcarboxamide hydrochloride (compound 24a) and (1R, 2S, 2'S)-1-phenyl-2-(1-aminopropyl)-cyclopropane N,N-diethylcarboxamide hydrochloride (compound 24b)

Compounds 23a and 23b (each, 1.7 mmol) obtained in Example 7 were individually treated in the same manner as in Example 6. As a result, compound 24a (yield: 80%) and compound 24b (yield: 83%) were obtained, both as a white powdery product.

The process for the production of compounds of the present invention (compounds 23a and 23b) and acid addition salts thereof of the present invention (compounds 24a and 24b) from the intermediate products (alcohols; compounds 16a and 16b) obtained in Reference Example 12, which process is described in the above-mentioned Reference Examples 14 to 16 and Examples 7 and 8, is illustrated in the following flow sheet.

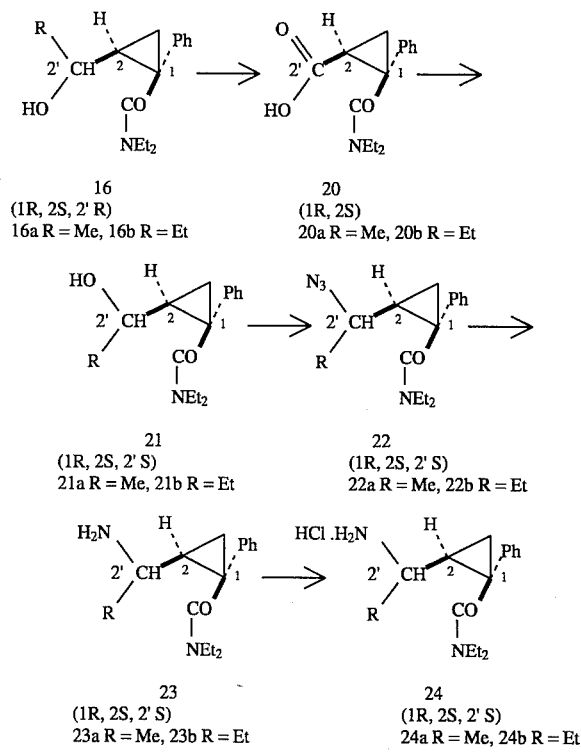

Flow sheet of the reactions conducted in Reference Examples 14 to 16 and Examples 7 to 8

The results of the nuclear magnetic resonance spectroscopic analysis of the products obtained in Reference Examples 14 to 16 and Examples 7 and 8 were, respectively, in agreement with the results, shown in Table 2 below, of the nuclear magnetic resonance spectroscopic analysis of the products obtained in Reference Examples 6 to 8 and Examples 3 and 4.

Reference Example 17 (production of a lactone from a racemic modification of epichlorohydrin as a starting material), Reference Example 18 (production of a hydroxymethyl from the lactone), Reference Example 19 (production of an aldehyde from the hydroxymethyl), Reference Example 20 (production of an alcohol from the aldehyde), Reference Example 21 (production of an azide from the alcohol), Example 9 [production of compounds of the present invention (compounds 30a and 30b) from the azide]and Example 10 [production of acid addition salts of the present invention (compounds 31a and 31b) from compounds 30a and 30b, respectively] are shown below.

REFERENCE EXAMPLE 17

Production of (1S, 2R )-1-phenyl-2-hydroxymethylcyclopropane carboxylic anhydride (compound 25)

8.58 g (0.22 mol ) of sodium amide was suspended in 40 ml of anhydrous benzene, to thereby obtain a suspension. To the obtained suspension was dropwise added a solution of 11.5 ml (0.10 mol) of phenylacetonitrile in 20 ml of anhydrous benzene in a stream of argon gas at 0° C. Then, the resultant mixture was stirred at room temperature for 3 hours, to thereby effect a reaction. To the reaction mixture was dropwise added a solution of 6.8 ml (0.087 mol) of a racemic modification of epichlorohydrin in 20 ml of anhydrous benzene while cooling with ice. Then, the resultant mixture was stirred at room temperature for 2 hours to thereby effect a reaction. After completion of the reaction, the reaction mixture was subjected to distillation under reduced pressure to thereby remove the solvent and obtain a residue. To the obtained residue were added 20 ml of ethanol and 10 ml of an aqueous 1N-KOH solution to thereby obtain a mixture. The mixture was refluxed for 15 hours. After that period of time, 12N hydrochloric acid was added to the resultant mixture while cooling with ice to thereby acidify the mixture. The acidified mixture was concentrated under reduced pressure to thereby obtain a residue. A saturated aqueous sodium hydrogencarbonate solution was added to the obtained residue, and ethyl acetate was further added for extraction to obtain an organic layer. The organic layer was separated, washed with saturated saline, dried over anhydrous sodium sulfate, and subjected to distillation under reduced pressure to thereby remove the solvent and obtain a residue. The obtained residue was purified by silica gel column chromatography (the composition of the developing solvent was; ethyl acetate:hexane=1:3). As a result, compound 25 (yield: 60%) was obtained as an orange oily product.

REFERENCE EXAMPLE 18

Production of (1S, 2R)-1-phenyl-2-hydroxymethylcyclopropane N,N-diethylcarboxamide (compound 26)

1.7 ml (16 mmol) of diethylamine was dissolved in 20 ml of anhydrous tetrahydrofuran. To the resultant solution was dropwise added 11 ml (16 mmol) of a solution of 1.64M butyllithium in hexane in a stream of argon gas at 0° C., to thereby obtain a solution of lithium diethylamine. To the obtained solution was dropwise added a solution of 1.7 g (10 mmol) of compound 25 obtained in Reference Example 17 in 20 ml of anhydrous tetrahydrofuran in a stream of argon gas at −78° C. to thereby obtain a mixture. Then, the obtained mixture was stirred at −78° C. for 2 hours to thereby effect a reaction. To the obtained mixture was added a saturated aqueous ammonium chloride solution to thereby terminate the reaction and then, the resultant mixture was subjected to distillation under reduced pressure to thereby remove the solvent and obtain a residue. Water was added to the obtained residue, and ethyl acetate was further added for extraction to obtain an organic layer. The organic layer was separated, washed with saturated saline, dried over anhydrous sodium sulfate, and concentrated under reduced pressure to thereby obtain a residue. The obtained residue was purified by silica gel column chromatography (the composition of the developing solvent was; ethyl acetate:hexane= 1:1). As a result, compound 26 (yield: 88%) was obtained as a yellow oily product.

REFERENCE EXAMPLE 19

Production of (1S, 2R)-1-phenyl-2-formylcyclopropane N,N-diethylcarboxamide (compound 27)

0.55 ml (6.40 mmol) of oxalylchloride was dissolved in 4 ml of anhydrous dichloromethane. To the resultant solution was dropwise added a solution of 0.91 ml (12.8 mmol) of dimethylsulfoxide in 4 ml of anhydrous dichloromethane in a stream of argon gas at −78° C., and the resultant mixture was stirred for 30 minutes. To the mixture was dropwise added a solution of 805 mg (3.26 mmol) of compound 26 obtained in Reference Example 18 in 4 ml of anhydrous dichloromethane, and the resultant mixture was stirred for 2 hours to effect a reaction. To the reaction mixture was added 1.9 ml (25.6 mmol) of triethylamine, and the resultant mixture was stirred for 1 hour to effect a reaction. To the obtained mixture was added a saturated aqueous ammonium chloride solution to thereby terminate the reaction. To the obtained reaction mixture was added chloroform for extraction to obtain an organic layer. The organic layer was separated, washed with saturated saline, dried over anhydrous sodium sulfate, and concentrated under reduced pressure to thereby obtain a residue. The obtained residue was purified by silica gel column chromatography (the composition of the developing solvent was; ethyl acetate:hexane= 2:1). As a result, compound 27 (yield: 99%) was obtained as a white crystalline product.

REFERENCE EXAMPLE 20

Production of (1S, 2R, 2'S)-1-phenyl-2-(1-hydroxyethyl)-cyclopropane N,N-diethylcarboxamide (compound 28a) and (1S, 2R, 2'S)-1-phenyl-2-(1-hydroxypropyl)-cyclopropane N,N-diethylcarboxamide (compound 28b)

Compound 27 (6.5 mmol) obtained in Reference Example 19 was dissolved in 40 ml of anhydrous tetrahydrofuran. To the resultant solution were individually added Grignard reagents (13 mmol of $CH_3MgBr$ and 13 mmol of $C_2H_5MgBr$) in a stream of argon gas at −20° C., and each of the resultant mixtures was stirred for 2 hours to effect a reaction. To each of the obtained mixtures was added a saturated aqueous ammonium chloride solution to thereby terminate the reaction and then, the resultant mixture was subjected to distillation under reduced pressure to thereby remove the solvent and obtain a residue. Water was added to each of the obtained residues, and ethyl acetate was further added for extraction to obtain an organic layer. Each of the organic layers was separated, washed with saturated saline, dried over anhydrous sodium sulfate, and concentrated under reduced pressure to thereby obtain a residue. Each of the obtained residues was purified by silica gel column chromatography (the composition of the developing solvent was; ethyl acetate:hexane=1:2). As a result, compound 28a (yield: 93%) was obtained when CH₃MgBr was used as Grignard reagent, and compound 28b (yield: 98%) was obtained when C₂H₅MgBr was used as Grignard reagent.

REFERENCE EXAMPLE 21

Production of (1S, 2R, 2'S)-1-phenyl-2-(1-azidoethyl)-N,N-diethylcyclopropane carboxamide (compound 29a) and (1S, 2R, 2'S)-1-phenyl-2-(1-azidopropyl)-N,N-diethylcyclopropane carboxamide (compound 29b)

Compounds 28a and 28b (each, 3.8 mmol) obtained in Reference Example 20 were individually dissolved in 10 ml of dimethylformamide. To each of the resultant solutions were added sodium azide (72 mmol), triphenylphosphine (11 mmol) and carbon tetrabromide (11 mmol) in this order while cooling with ice. Then, the temperature of each of the resultant mixtures was allowed to return to room temperature, and each of the mixtures was stirred for 3 hours to effect a reaction. After completion of the reaction, each of the resultant reaction mixtures was subjected to distillation under reduced pressure to thereby remove the solvent and obtain a residue. Water was added to each of the obtained residues, and ethyl acetate was further added for extraction to obtain an organic layer. Each of the organic layers was separated, washed with saturated saline, dried over anhydrous sodium sulfate, and concentrated under reduced pressure to thereby obtain a residue. Each of the obtained residues was purified by silica gel column chromatography (the composition of the developing solvent for the residue obtained from compound 28a was; ethyl acetate:hexane= 1:5, and the composition of the developing solvent for the residue obtained from compound 28b was; ethyl acetate:hexane=1:9). As a result, compound 29a (yield: 67%) was obtained from compound 28a and compound 29b (yield: 63%) was obtained from compound 28b.

EXAMPLE 9

Production of (1S, 2R, 2'S)-1-phenyl-2-(1-aminoethyl)-cyclopropane N,N-diethylcarboxamide (compound 30a) and (1S, 2R, 2'S)-1-phenyl-2-(1-aminopropyl)-cyclopropane N,N-diethylcarboxamide (compound 30b)

Compounds 29a and 29b (each, 2.1 mmol) obtained in Reference Example 21 were individually dissolved in 10 ml of methanol. To each of the resultant solutions was added 44 mg of 10% Pd-carbon, and each of the resultant mixtures was stirred at room temperature for 1 hour in a hydrogen gas atmosphere. Each of the resultant reaction mixtures was subjected to filtration by means of Celite, and each of the resultant filtrates was concentrated under reduced pressure to thereby obtain a residue. Each of the residue was purified by silica gel column chromatography (the composition of the developing solvent for the residue obtained from compound 29a was; chloroform:methanol:aqueous ammonia= 10:1:0.2 and the composition of the developing solvent for the residue obtained from compound 29b was; chloroform:methanol:aqueous ammonia water=65:25:1:2). As a result, compound 30a (yield: 83%) was obtained from compound 29a, and compound 30b (yield: 95%) was obtained from compound 29b.

EXAMPLE 10

Production of (1S, 2R, 2'S)-1-phenyl-2-(1-aminoethyl)-cyclopropane N,N-diethylcarboxamide hydrochloride (compound 31a) and (1S, 2R, 2'S)-1-phenyl-2-(1-aminopropyl)-cyclopropane N,N-diethylcarboxamide hydrochloride (compound 31b)

Diaion WA-30 (ion exchange resin manufactured and sold by Mitsubishi Chemical Industries, Ltd., Japan) was treated with an aqueous 1N-NaOH solution and washed with distilled water to thereby render neutral the resin. The resin was further treated with 1N hydrochloric acid and washed with distilled water to thereby render neutral the resin. The resultant resin was used in the purification of compounds described below.

Compounds 30a and 30b (each, 1.7 mmol) obtained in Example 9 were individually dissolved in chloroform. To each of the resultant solutions was added an aqueous 1N-NaOH solution to thereby obtain an organic layer. Each of the organic layers was separated, washed with saturated saline, dried over anhydrous sodium sulfate, and subjected to distillation under reduced pressure to thereby remove the solvent and obtain a residue. Each of the obtained residues was individually dissolved in methanol, and the resultant solution was applied to a column packed with the above-prepared ion exchange resin and eluted with methanol. Each of the eluates was concentrated under reduced pressure to thereby obtain crystals. The crystals obtained from the respective eluates were washed with diethyl ether. As a result, compound 31a (yield: 66%) was obtained from compound 30a, and compound 31b (yield: 92%) was obtained from compound 30b, both as a white powdery product.

The process for the production of compounds of the present invention (compounds 30a and 30b) and acid addition salts thereof of the present invention (compounds 31a and 31b) from a racemic modification of epichlorohydrin as a starting material, which process is described in the above-mentioned Reference Examples 17 to 21 and Examples 9 and 10, is illustrated in the following flow sheet.

Flow sheet of the reactions conducted in Reference Examples 17 to 21 and Examples 9 and 10

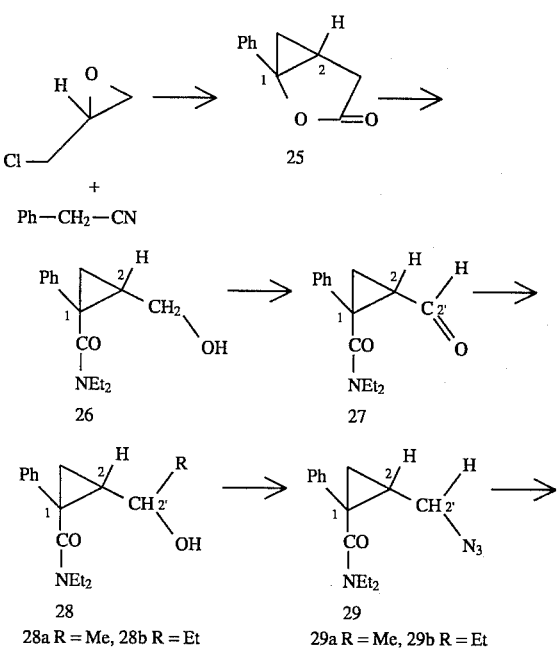

-continued
Flow sheet of the reactions conducted in Reference
Examples 17 to 21 and Examples 9 and 10

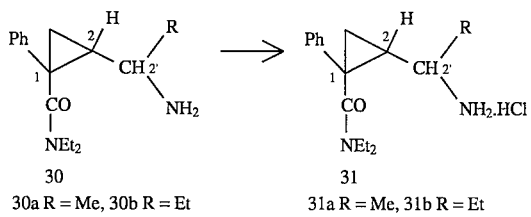

30  
30a R = Me, 30b R = Et 31  
31a R = Me, 31b R = Et

The results of the nuclear magnetic resonance spectroscopic analysis of the products obtained in Reference Examples 17 to 21 and Examples 9 and 10 were, respectively, in agreement with the results, shown in Table 2 below, of the nuclear magnetic resonance spectroscopic analysis of the products obtained in Reference Examples 1 to 5 and Examples 1 and 2.

Reference Example 22 (production of an alcohol from the aldehyde obtained in Reference Example 3), Reference Example 23 (production of an azide from the alcohol), Example 11 [production of compounds of the present invention (compounds 6c and 6d) from the azide] and Example 12 [production of acid addition salts of the present invention (compounds 7c and 7d) from compounds 6c and 6d, respectively] are shown below.

REFERENCE EXAMPLE 22

Production of (1S, 2R, 2's)-1-phenyl-2-(1-hydroxybutyl)-cyclopropane N,N-diethylcarboxamide (compound 4c) and (1S, 2R, 2'S)-1-phenyl-2-(1-hydroxyisopentyl)-cyclopropane N,N-diethylcarboxamide (compound 4d)

Compound 3 (1.60 mmol) obtained in Reference Example 3 was dissolved in 10 ml of anhydrous tetrahydrofuran. To the resultant solution were individually added Grignard reagents (3.20 mmol of $C_3H_7MgBr$ and 3.20 mmol of iso-$C_4H_9MgBr$) in a stream of argon gas at −20° C., and each of the resultant mixtures was stirred for 2 hours to effect a reaction. To each of the obtained mixtures was added a saturated aqueous ammonium chloride solution to thereby terminate the reaction and then, the resultant mixture was subjected to distillation under reduced pressure to thereby remove the solvent and obtain a residue. Water was added to each of the obtained residues, and ethyl acetate was further added for extraction to obtain an organic layer. Each of the organic layers was separated, washed with saturated saline, dried over anhydrous sodium sulfate, and concentrated under reduced pressure to thereby obtain a residue. Each of the obtained residues was purified by silica gel column chromatography (the composition of the developing solvent was; ethyl acetate:hexane=1:2). As a result, compound 4c (yield: 87%) was obtained when $C_3H_7MgBr$ was used as Grignard reagent, and compound 4d (yield: 88%) was obtained when iso-$C_4H_9MgBr$ was used as Grignard reagent.

REFERENCE EXAMPLE 23

Production of (1S, 2R, 2'S)-1-phenyl-2-(1-azidobutyl)-N,N-diethylcyclopropane carboxamide (compound 5c) and (1S, 2R, 2'S)-1-phenyl-2-(1-azidoisopentyl)-N,N-diethylcyclopropane carboxamide (compound 5d)

Compounds 4c and 4d (each, 1.03 mmol) obtained in Reference Example 22 were individually dissolved in 3 ml of dimethylformamide. To each of the resultant solutions were added sodium azide (19.6 mmol), triphenylphosphine (3.09 mmol) and carbon tetrabromide (3.09 mmol) in this order while cooling with ice. Then, the temperature of each of the resultant mixtures was allowed to return to room temperature, and each of the mixtures was stirred for 3 hours to effect a reaction. After completion of the reaction, each of the resultant reaction mixtures was subjected to distillation under reduced pressure to thereby remove the solvent and obtain a residue. Water was added to each of the obtained residues, and ethyl acetate was further added for extraction to obtain an organic layer. Each of the organic layers was separated, washed with saturated saline, dried over anhydrous sodium sulfate, and concentrated under reduced pressure to thereby obtain a residue. Each of the obtained residues was purified by silica gel column chromatography (the composition of the developing solvent was; ethyl acetate:hexane=1:9). As a result, compound 5c (yield: 67%) was obtained from compound 4c and compound 5d (yield: 94%) was obtained from compound 4d.

EXAMPLE 11

Production of (1S, 2R, 2'S)-1-phenyl-2-(1-aminobutyl)-cyclopropane N,N-diethylcarboxamide (compound 6c) and (1S, 2R, 2'S)-1-phenyl-2-(1-aminoisopentyl)-cyclopropane N,N-diethylcarboxamide (compound 6d)

Compounds 5c and 5d (each, 0.476 mmol) obtained in Reference Example 23 were individually dissolved in 5 ml of methanol. To each of the resultant solutions was added 50 mg of 10% Pd-carbon, and each of the resultant mixtures was stirred for 1 hour at room temperature in a hydrogen gas atmosphere. Each of the resultant reaction mixtures was subjected to filtration by means of Celite, and each of the resultant filtrates was concentrated under reduced pressure to thereby obtain a residue. Each of the residues was purified by silica gel column chromatography (the composition of the developing solvent was; chloroform:methanol:aqueous ammonia:water=65:25:1:2). As a result, compound 6c (yield: 99%) was obtained from compound 5c and compound 6d (yield: 51%) was obtained from compound 5d.

EXAMPLE 12

Production of (1S, 2R, 2'S)-1-phenyl-2-(1-aminobutyl)-cyclopropane N,N-diethylcarboxamide hydrochloride (compound 7c) and (1S, 2R, 2'S)-1-phenyl-2-(1-aminoisopentyl)-cyclopropane N,N-diethylcarboxamide hydrochloride (compound 7d)

Diaion WA-30 (ion exchange resin manufactured and sold by Mitsubishi Chemical Industries, Ltd., Japan) was treated with an aqueous 1N-NaOH solution and washed with distilled water to thereby render neutral the resin. The resin was further treated with 1N hydrochloric acid and washed with distilled water to thereby render neutral the resin. The resultant resin was used in the purification of compounds described below.

Compounds 6c and 6d (each, 0,329 mmol) obtained in Example 11 were individually dissolved in chloroform. To each of the resultant solutions was added an aqueous 1N-NaOH solution to thereby obtain an organic layer. Each of the organic layers was separated, washed with saturated saline, dried over anhydrous sodium sulfate, and subjected to distillation under reduced pressure to thereby remove the solvent and obtain a residue. Each of the obtained residues was individually dissolved in methanol, and the resultant solution was applied to a column packed with the above-prepared ion exchange resin and eluted with methanol. Each of the eluates was concentrated under reduced pressure to thereby obtain crystals. The crystals obtained from the respective eluates were washed with diethyl ether. As a result, compound 7c (yield: 96%) was obtained from compound 6c, and compound 7d (yield: 86%) was obtained from compound 6d, both as a white powdery product.

The process for the production of compounds of the present invention (compounds 6c and 6d) and acid addition salts thereof of the present invention (compounds 7c and 7d) from the intermediate product (aldehyde; compound 3) obtained in Reference Example 3, which process is described in the above-mentioned Reference Examples 22 and 23 and Examples 11 and 12, is included in the above-shown flow sheet of the reactions conducted in Reference Examples 1 to 5 and Examples 1 and 2.

The results of the nuclear magnetic resonance spectroscopic analysis of the products obtained in Reference Examples 22 and 23 and Examples 11 and 12 are shown in Table 2 below.

Reference Example 24 (production of an alcohol from the aldehyde obtained in Reference Example 3), Reference Example 25 (production of an azide from the alcohol), Example 13 [production of a compound of the present invention (compound 6e) from the azide]and Example 14 [production of an acid addition salt of the present invention (compound 7e) from compound 6e] are shown below.

REFERENCE EXAMPLE 24

Production of (1S, 2R, 2'R)-1-phenyl-2-(1-hydroxybenzyl)-cyclopropane N,N-diethylcarboxamide (compound 4e)

Compound 3 (1.20 mmol) obtained in Reference Example 3 was dissolved in 10 ml of anhydrous tetrahydrofuran. To the resultant solution was added Grignard reagent (2.40 mmol of phenyl MgBr) in a stream of argon gas at −20° C., and the resultant mixture was stirred for 2 hours to effect a reaction. To the resultant reaction mixture was added a saturated aqueous ammonium chloride solution to thereby terminate the reaction and then, the resultant mixture was subjected to distillation under reduced pressure to thereby remove the solvent and obtain a residue. Water was added to the obtained residue, and ethyl acetate was further added for extraction to obtain an organic layer. The organic layer was separated, washed with saturated saline, dried over anhydrous sodium sulfate, and concentrated under reduced pressure to thereby obtain a residue. The obtained residue was purified by silica gel column chromatography (the composition of the developing solvent was; ethyl acetate:hexane= 1:2). As a result, compound 4e (yield: 86%) was obtained.

REFERENCE EXAMPLE 25

Production of (1S, 2R, 2'R)-1-phenyl-2-(1-azidobenzyl)-N,N-diethylcyclopropane carboxamide (compound 5e)

Compound 4e (0.80 mmol) obtained in Reference Example 24 was dissolved in 3 ml of dimethylformamide. To the resultant solution were added sodium azide (15.2 mmol), triphenylphosphine (2.40 mmol) and carbon tetrabromide (2.40 mmol) in this order while cooling with ice. Then, the temperature of the resultant mixture was allowed to return to room temperature, and the mixture was stirred for 3 hours to effect a reaction. After completion of the reaction, the resultant reaction mixture was subjected to distillation under reduced pressure to thereby remove the solvent and obtain a residue. Water was added to the obtained residue, and ethyl acetate was further added for extraction to obtain an organic layer. The organic layer was separated, washed with saturated saline, dried over anhydrous sodium sulfate, and concentrated under reduced pressure to thereby obtain a residue. The obtained residue was purified by silica gel column chromatography (the composition of the developing solvent was; ethyl acetate:hexane= 1:9). As a result, compound 5e (0.63 mmol, yield: 79%) was obtained.

EXAMPLE 13

Production of (1S, 2R, 2'R)-1-phenyl-2-(1-aminobenzyl)-cyclopropane N,N-diethylcarboxamide (compound 6e)

Compound 5e (0.44 mmol) obtained in Reference Example 25 was dissolved in 5 ml of methanol. To the resultant solution was added 50 mg of 10% Pd-carbon, and the resultant mixture was stirred at room temperature for 1 hour in a hydrogen gas atmosphere. The resultant reaction mixture was subjected to filtration by means of Celite, and the resultant filtrate was concentrated under reduced pressure to thereby obtain a residue. The residue was purified by silica gel column chromatography (the composition of the developing solvent was; chloroform:methanol:aqueous ammonia:water=65:25:1:2). As a result, compound 6e (0.41 mmol, yield: 99%) Was obtained.

EXAMPLE 14

Production of (1S, 2R, 2'R)-1-phenyl-2-(1-aminobenzyl)-cyclopropane N,N-diethylcarboxamide hydrochloride (compound 7e)

Diaion WA-30 (ion exchange resin manufactured and sold by Mitsubishi Chemical Industries, Ltd., Japan) was treated with an aqueous 1N-NaOH solution and washed with distilled water to thereby render neutral the resin. The resin was further treated with 1N hydrochloric acid and washed with distilled water to thereby render neutral the resin. The resultant resin was used in the purification of a compound described below.

Compound 6e (0.21 mmol) obtained in Example 13 was dissolved in chloroform. To the resultant solution was added an aqueous 1N-NaOH solution to thereby obtain an organic layer. The organic layer was separated, washed with saturated saline, dried over anhydrous sodium sulfate, and subjected to distillation under reduced pressure to thereby remove the solvent and obtain a residue. The obtained residue was dissolved in methanol, and the resultant solution was applied to a column packed with the above-prepared ion exchange resin and eluted with methanol. The eluate was concentrated under reduced pressure to thereby obtain crystals. The obtained crystals were washed with diethyl ether. As a result, compound 7e (0.18 mmol, yield: 86%) was obtained as a white powdery product.

The process for the production of a compound of the present invention (compound 6e) and an acid addition salt thereof of the present invention (compound 7e) from the intermediate product (aldehyde; compound 3) obtained in Reference Example 3, which process is described in the above-mentioned Reference Examples 24 and 25 and Examples 13 and 14, is included in the above-shown flow sheet of the reactions conducted in Reference Examples 1 to 5 and Examples 1 and 2.

The results of the nucleic magnetic resonance spectroscopic analysis of the products obtained in the above-mentioned Reference Examples 24 and 25 and Examples 13 and 14 are shown in Table 2 below.

The process for the production of a compound of the present invention (compound 6f) wherein R of formula (1) is a vinyl group, and an acid addition salt thereof of the present invention (compound 7f) from compound 3 (aldehyde) obtained in Reference Example 3 as a starting material is shown below.

REFERENCE EXAMPLE 26

Production of (1S, 2R, 2'S)-1-phenyl-2-(1-hydroxy-2-ethoxycarbonylethyl)-cyclopropane N,N-diethylcarboxamide (compound 32a) and (1S, 2R, 2'R)-1-phenyl-2-(1-hydroxy-2-ethoxycarbonylethyl)-cyclopropane N,N-diethylcarboxamide (compound 32b)

3.93 ml (18.6 mmol) of hexamethyldisilazane was dissolved in 20 ml of anhydrous THF. To the resultant solution was added 11.2 ml (18.3 mmol) of a solution of 1.66M butyllithium in hexane in a stream of argon gas at −10° C., and the resultant mixture was stirred for 20 minutes. 1.86 ml (18.6 mmol) of anhydrous ethyl acetate was added to the mixture at −78° C., and the resultant mixture was stirred for 20 minutes. A solution of 3.8 g (15.5 mmol) of compound 3 obtained in Reference Example 3 in 20 ml of anhydrous THF was dropwise added to the mixture and the resultant mixture was stirred at −78° C. for 2 hours to effect a reaction. To the obtained mixture was added a saturated aqueous ammonium chloride solution to thereby terminate the reaction and then, the resultant mixture was concentrated under reduced pressure to thereby obtain a residue. Water was added to the obtained residue, and ethyl acetate was further added for extraction to obtain an organic layer. The organic layer was separated, washed with saturated saline, dried over anhydrous sodium sulfate, and concentrated under reduced pressure to thereby obtain a residue. The obtained residue was purified by silica gel column chromatography (the composition of the developing solvent was; ethyl acetate:hexane=2:1 to 1:2). As a result, 4.1 g of compound 32a (12.3 mmol, yield: 79%) was obtained as a colorless oily product and 485 mg of compound 32b (1.46 mmol, yield: 9.4%) was obtained as a yellow crystalline product.

REFERENCE EXAMPLE 27

Production of (1S, 2R, 2'S)-1-phenyl-2-(1,3-dihydroxypropyl)-cyclopropane N,N-diethylcarboxamide (compound 33)

3.9? g (11.9 mmol) of compound 32a obtained in Reference Example 26 was dissolved in 40 ml of methanol. To the resultant solution was gradually added 4.50 g (119 mmol) of $NaBH_4$ at room temperature, and the resultant mixture was stirred for 2 hours and heated under reflux for 1 hour to thereby effect a reaction. To the resultant reaction mixture was added acetic acid to thereby terminate the reaction and then, the resultant mixture was concentrated under reduced pressure to thereby obtain a residue. Water was added to the obtained residue, and ethyl acetate was further added for extraction to obtain an organic layer. The organic layer was separated, washed with saturated saline, dried over anhydrous sodium sulfate, and concentrated under reduced pressure to thereby obtain a residue. The obtained residue was purified by silica gel column chromatography (the composition of the developing solvent was; chloroform:methanol=6:1). As a result, 3.40 g of compound 33 (11.7 mmol, yield: 98%) was obtained as a white crystalline product.

REFERENCE EXAMPLE 28

Production of (1S, 2R, 2'S)-1-phenyl-2-(1-hydroxy-3-pivaloyl oxypropyl)-cyclopropane N,N-diethylcarboxamide (compound 34)

1.60 g (5.50 mmol) of compound 33 obtained in Reference Example 27 was dissolved in 30 ml of anhydrous pyridine. To the resultant solution was added 1.26 ml (7.59 mmol) of pivaloyl chloride in a stream of argon gas while cooling with ice, and the resultant mixture was stirred for 1.5 hours while cooling with ice to thereby effect a reaction. Water was added to the resultant reaction mixture to thereby terminate the reaction. The reaction mixture was concentrated under reduced pressure to thereby obtain a residue. Water was added to the obtained residue, and ethyl acetate was further added for extraction to obtain an organic layer. The organic layer was separated, washed with saturated saline, dried over anhydrous sodium sulfate, and concentrated under reduced pressure to thereby obtain a residue. The obtained residue was purified by silica gel column chromatography (the composition of the developing solvent was; ethyl acetate:hexane=1:3). As a result, 1.81 g of compound 34 (4.83 mmol, yield: 88%) was obtained as a colorless oily product.

REFERENCE EXAMPLE 29

Production of (1S, 2R, 2'S)-1-phenyl-2-(1-azido-3-pivaloyl oxypropyl)-cyclopropane N,N-diethylcarboxamide (compound 35)

1.50 g (4.0 mmol) of compound 34 obtained in Reference Example 28 was dissolved in 35 ml of DMF. To the resultant solution were added 4.94 g (76 mmol) of sodium azide, 3.15 g (12 mmol) of triphenylphosphine and 3.98 g (12 mmol) of carbon tetrabromide in this order while cooling with ice. Then, the temperature of the resultant mixture was allowed to return to room temperature, and the mixture was stirred overnight to effect a reaction. After completion of the reaction, the resultant reaction mixture was concentrated under reduced pressure to thereby obtain a residue. Water was added to the obtained residue, and ethyl acetate was further added for extraction to obtain an organic layer. The organic layer was separated, washed with saturated saline, dried over anhydrous sodium sulfate, and concentrated under reduced pressure to thereby obtain a residue. The obtained residue was purified by silica gel column chromatography (the composition of the developing solvent was; ethyl acetate:hexane=1:4). As a result, 1.46 g of compound 35 (3.65 mmol, yield: 91%) was obtained as a colorless oily product.

REFERENCE EXAMPLE 30

Production of (1S, 2R, 2'S)-1-phenyl-2-(1-azido-3-hydroxypropyl)-cyclopropane N,N-diethylcarboxamide (compound 36)

1.33 g of compound 35 (3.33 mmol) obtained in Reference Example 29 was dissolved in 30 ml of anhydrous methanol. To the resultant solution was added 2.5 ml of 28% sodium methoxide in a stream of argon gas, and the resultant mixture was stirred at room temperature overnight to effect a reaction. To the obtained mixture was added acetic acid to thereby terminate the reaction and then, the resultant mixture was concentrated under reduced pressure to thereby obtain a residue. Water was added to the obtained residue, and ethyl acetate was further added for extraction to obtain an organic layer. The organic layer was separated, washed with saturated saline, dried over anhydrous sodium sulfate, and concentrated under reduced pressure to thereby obtain a residue. The obtained residue was purified by silica gel column chromatography (the composition of the developing solvent was; ethyl acetate:hexane=3:1). As a result, 1.04 g (3.29 mmol) of compound 36 (yield: 99%) was obtained as a white crystalline product.

REFERENCE EXAMPLE 31

Production of (1S, 2R, 2'S)-1-phenyl-2-(1-azido-3-tosyloxypropyl)-cyclopropane N,N-diethylcarboxamide (compound 37)

400 g of compound 36 (1.27 mmol) obtained in Reference Example 30 was dissolved in anhydrous dichloromethane. To the resultant solution were added 20 mg of dimethylaminopyridine, 0.89 ml (6.36 mmol) of triethylamine, and 606 mg (3.18 mmol) of tosylchloride in this order at room temperature. Then, the resultant mixture was stirred at room temperature overnight to effect a reaction. Water was added to the resultant reaction mixture, and dichloromethane was further added for extraction to obtain an organic layer. The organic layer was separated, washed with saturated saline, dried over anhydrous sodium sulfate, and concentrated under reduced pressure to thereby obtain a residue. The obtained residue was purified by silica gel column chromatography (the composition of the developing solvent was; ethyl acetate:hexane=1:3). As a result, 592 mg (1.26 mmol) of compound 37 (yield: 99%) was obtained as a colorless oily product.

REFERENCE EXAMPLE 32

Production of (1S, 2R, 2'S)-1-phenyl-2-(1-azido-3-phenylselenylpropyl)-cyclopropane N,N-diethylcarboxamide (compound 38)

165 mg (0.528 mmol) of diphenyl diselenide was dissolved in 8 ml of anhydrous ethanol. To the resultant solution was added 60 mg (1.58 mmol) of $NaBH_4$ in a stream of argon gas at room temperature. Then, the resultant mixture was stirred so that the mixture becomes transparent. To the mixture was added 190 mg (0.404 mmol) of compound 37 obtained in Reference Example 31 in 4 ml of anhydrous ethanol. The resultant mixture was stirred overnight to effect a reaction. Water was added to the resultant reaction mixture, and diethylether was further added for extraction to obtain an organic layer. The organic layer was separated, washed with saturated saline, dried over anhydrous sodium sulfate, and concentrated under reduced pressure to thereby obtain a residue. The obtained residue was purified by silica gel column chromatography (the composition of the developing solvent was; ethyl acetate:hexane= 1:5). As a result, 156 mg (0.342 mmol) of compound 38 was obtained (yield: 85%) as a colorless oily product.

REFERENCE EXAMPLE 33

Production of (1S, 2R, 2'S)-1-phenyl-2-(1-amino-3-phenylselenylpropyl)-cyclopropane N,N-diethylcarboxamide (compound 39)

80.0 mg (0.176 mmol) of compound 38 obtained in Reference Example 32 was dissolved in 2 ml of pyridine. To the resultant mixture was added 180 mg (0.264 mmol) of triphenylphosphin, and the resultant mixture was stirred at room temperature for 5 hours to effect a reaction. 2 ml of 28% aqueous ammonia was added to the reaction mixture and the resultant mixture was stirred at room temperature overnight to effect a reaction. The resultant reaction mixture was concentrated under reduced pressure to obtain a residue. Water was added to the obtained residue, and ethyl acetate was further added for extraction to obtain an organic layer. The organic layer was separated, washed with saturated saline, dried over anhydrous sodium sulfate, and concentrated under reduced pressure to thereby obtain a residue. The obtained residue was purified by silica gel column chromatography (the composition of the developing solvent was; chloroform:methanol: 28% aqueous ammonia= 90:10:0.2). As a result, 70 mg (0.163 mmol) of compound 39 (yield: 93%) was obtained as a colorless oily product.

REFERENCE EXAMPLE 34

Production of (1S, 2R, 2'S)-1-phenyl-2-(1-t-butoxycarbonylamino-3-phenylselenylpropyl)-cyclopropane N,N-diethylcarboxamide (compound 40)

960 mg (2.11 mmol) of compound 39 obtained in Reference Example 33 was dissolved in 35 ml of anhydrous dichloromethane. To the resultant solution was added 1.27 g (5.58 mmol) of di-t-butyldicarbonate in a stream of argon gas. The resultant mixture was stirred at room temperature for 5 hours to effect a reaction. Water was added to the resultant reaction mixture, and dichloromethane was further added for extraction to obtain an organic layer. The organic layer was separated, washed with saturated saline, dried over anhydrous sodium sulfate, and concentrated under reduced pressure to thereby obtain a residue. The obtained residue was purified by silica gel column chromatography (the composition of the developing solvent was; ethyl acetate:hexane=1:3). As a result, 1.02 g (1.92 mmol) of compound 40 (yield: 92%) was obtained as a white crystalline product.

REFERENCE EXAMPLE 35

Production of (1S, 2R, 2'S)-1-phenyl-2-(1-t-butoxycarbonylamino-2-propenyl)-cyclopropane N,N-diethylcarboxamide (compound 41)

135 mg of compound 40 (0.255 mmol) obtained in Reference Example 34 was dissolved in 6 ml of THF. To the resultant solution was added a 30% aqueous hydrogen peroxide solution, stirred at room temperature for 6 days to effect a reaction. Water was added to the resultant reaction mixture, and dichloromethane was further added for extraction to obtain an organic layer. The organic layer was separated, washed with saturated saline, dried over anhydrous sodium sulfate, and concentrated under reduced pressure to thereby obtain a residue. The obtained residue was purified by silica gel column chromatography (the composition of the developing solvent was; chloroform:methanol= 20:1). As a result, 80 mg (0.215 mmol) of compound 41 (yield: 84%) was obtained as a white crystalline product.

EXAMPLE 15

Production of (1S, 2R, 2'S)-1-phenyl-2-(1-amino-2-propenyl)-cyclopropane N,N-diethylcarboxamide (compound 6f)

100 mg (0.268 mmol) of compound 41 obtained in Reference Example 35 was dissolved in 4.5 ml of methanol. To the resultant solution was added 3 ml of 90% trifluoroacetic acid, the resultant mixture was stirred at room temperature overnight to effect a reaction. To the resultant reaction mixture was added an aqueous 3N sodium hydroxide solution to thereby alkalify the reaction mixture, and dichloromethane was further added for extraction to obtain an organic layer. The organic layer was separated, washed with saturated saline, dried over anhydrous sodium sulfate, and concentrated under reduced pressure to thereby obtain a residue. The obtained residue was purified by silica gel column chromatography (the composition of the developing solvent was; chloroform:methanol: 28% aqueous ammonia= 80:20:0.2). As a result, 40 mg (0.147 mmol) of compound 6f (yield: 55%) was obtained as a brown oily product.

EXAMPLE 16

Production of (1S, 2R, 2'S)-1-phenyl-2-(1-amino-2-propenyl)-cyclopropane N,N-diethylcarboxamide hydrochloride (compound 7f)

Diaion WA-30 (ion exchange resin manufactured and sold by Mitsubishi Chemical Industries, Ltd., Japan) was treated with an aqueous 1N-NaOH solution and washed with distilled water to thereby render neutral the resin. The resin was further treated with 1N hydrochloric acid and washed with distilled water to thereby render neutral the resin. The resultant resin was used in the purification of compounds described below. 30 mg (0.110 mmol) of compound 41 obtained in Reference Example 35 was dissolved in methanol, and the resultant solution was applied to a column packed with the above-prepared ion exchange resin and eluted with methanol. The eluate was concentrated under reduced pressure to thereby obtain crystals. The obtained crystals were washed with diethyl ether. As a result, 30 mg (0.0974 mmol) of compound 7f (yield: 89%) was obtained as a white powdery product.

The process for the production of compound of the present invention (compound 6f) and an acid addition salt thereof (compound 7f) from the intermediate product (aldehyde; compound 3) obtained in Reference Example 3, which process is described in Reference Examples 26 to 35 and Examples 15 and 16, is illustrated in the following flowsheet.

Flow sheet of the reactions conducted in Reference Examples 26 to 35 and Examples 15 to 16

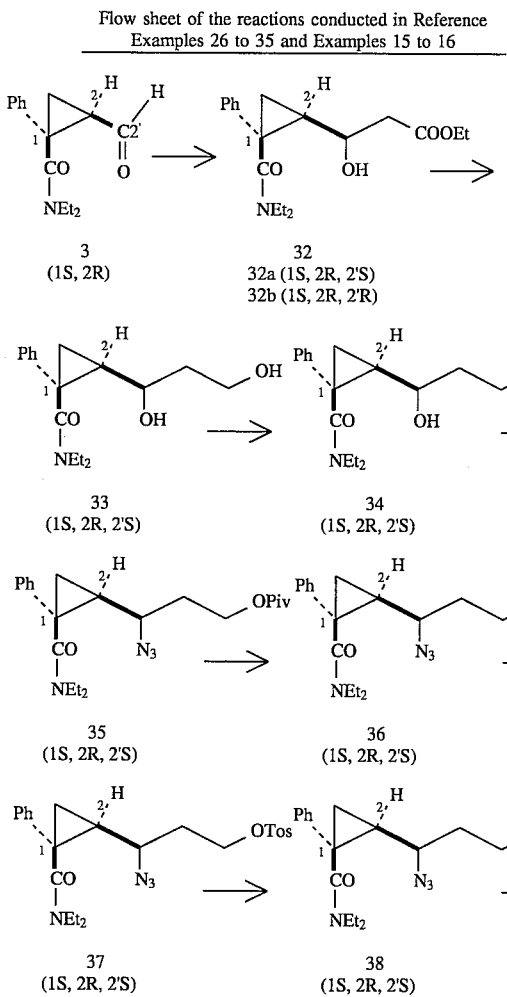

-continued
Flow sheet of the reactions conducted in Reference Examples 26 to 35 and Examples 15 to 16

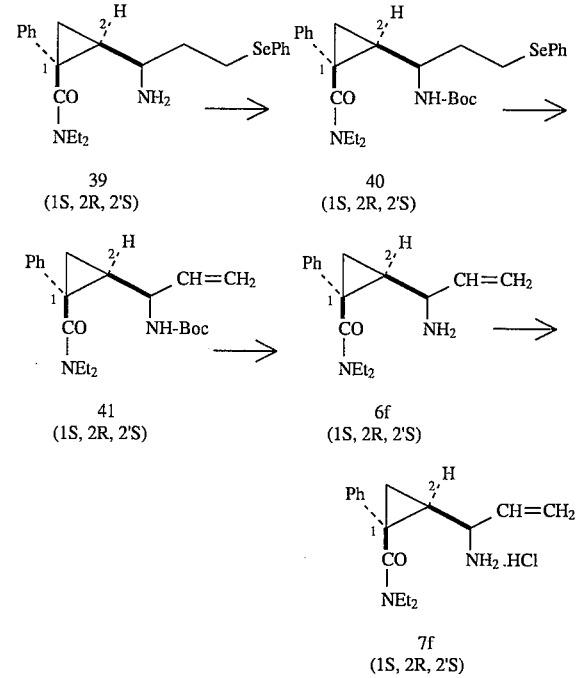

The results of the nuclear magnetic resonance spectroscopic analysis of the products obtained in Reference Examples 26 to 35 and Example 15 and 16 are shown in Table 3 below.

TABLE 2

| Compound | $^1$H-NMR (CDCl$_3$) δ: |
|---|---|
| 1 | (100MHz)1.35(1H, dd, J=4.6Hz, 4.9Hz), 1.64(1H, dd, J=4.9Hz, 7.7Hz), 2.55(1H, ddd, J=4.4Hz, 4.6Hz, 7.7Hz), 4.27(1H, d, J=9.0Hz), 4.47(1H, dd, J=4.4Hz, 9.0Hz), 7.34(5H, m) |
| 2 | (400MHz)0.91(3H, t, J=7.3Hz), 1.08(1H, dd, J=4.9Hz, 6.3Hz), 1.14(3H, t, J=7.3Hz), 1.55(1H, dddd, J=4.9Hz, 6.3Hz, 8.8Hz, 10.3Hz), 1.65(1H, dd, J=4.9Hz, 8.8Hz), 3.17(1H, ddd, J=2.4Hz, 10.3Hz, 12.2Hz), 3.32–3.56(4H, m), 4.40(1H, ddd, J=4.9Hz, 11.2Hz, 12.2Hz), 4.74(1H, dd, J=2.4Hz, 11.2Hz), 7.19–7.32(5H, m) |
| 3 | (270MHz)0.69(3H, t, J=7.1Hz), 1.11(3H, t, J=7.1Hz), 1.71(1H, dd, J=5.5Hz, 8.5Hz), 2.28(1H, dd, J=5.5Hz, 6.0Hz), 2.50(1H, ddd, J=6.0Hz, 6.0Hz, 8.5Hz), 3.12–3.52(4H, m), 7.23–7.38(5H, m), 9.05(1H, d, J=6.0Hz) |
| 4a | (400MHz)0.93(3H, t, J=7.3Hz), 1.03(1H, dd, J=5.8Hz, 6.1Hz), 1.14(3H, t, J=7.3Hz), 1.27(1H, m), 1.31(3H d, J=6.3Hz), 1.67(1H, dd, J=5.8Hz, 8.5Hz), 3.28–3.55(5H, m), 7.4(5H, m) |
| 4b | (400MHz)0.93(3H, t, J=7.1Hz), 1.00(3H, t, J=7.6Hz), 1.06(1H, dd, J=5.9Hz), 1.14(3H, t, J=7.1Hz), 1.26(1H, m), 1.67(3H, m), 3.07(1H, m), 3.33–3.55(4H, m), 7.15–7.31(5H, m) |
| 8a | (500MHz)0.87(3H, t, J=7.0Hz), 1.10(3H, t, J=7.0Hz), 1.65–1.67(1H, m), 2.21–2.26(1H, m), 2.39(3H, s), 2.44(1H, dd, J=7.0Hz, 7.0Hz), 3.22–3.29(2H, m), 3.38(1H, dq, J=7.0Hz, 14.0Hz), 3.45(1H, dq, J=7.0Hz, 14.0Hz), 7.26–7.35(5H, m) |
| 8b | (500MHz)0.88(3H, t, J=7.0Hz), 1.08(3H, |

TABLE 2-continued

| Compound | ¹H-NMR (CDCl₃) δ: |
|---|---|
| | t, J=7.0Hz), 1.14(3H, t, J=7.0Hz), 1.70(1H, dd, J=5.0Hz, 7.5Hz), 2.23(1H, dd, J=5.0Hz, 6.5Hz), 2.42(1H, dd, J=6.5Hz, 7.5Hz), 2.60(1H, dq, J=7.0Hz, 17.5Hz), 2.79(1H, dq, J=7.0Hz, 17.5Hz), 3.18-3.26(2H, m), 3.37-3.51(2H, m), 7.25-7.35(5H, m) |
| 9a | (500MHz)0.76(3H, t, J=7.0Hz), 1.12(3H, t, J=70Hz), 1.27(3H, d, −J=6.5Hz), 1.39-1.46(2H, m), 1.49-1.51(1H, m), 3.00(1H, brs), 3.23-3.35(2H, m), 3.41(1H, dq, J=7.0Hz, 14.0Hz), 3.48(1H, dq, J=7.0Hz, 14.0Hz), 7.20-7.30(5H, m) |
| 9b | (500MHz)0.75(3H, t, J=7.0Hz), 1.00(3H, t, J=7.5Hz), 1.12(3H, t, J=7.0Hz), 1.38-1.44(2H, m), 1.51-1.66(3H, m), 2.96(1H, brs), 3.26(1H, dq, J=7.0Hz, 14.0Hz), 3.31(1H, dq, −J=7.0Hz, 14.0Hz), 3.40(1H, dq, J=7.0Hz, 14.0Hz), 3.47(1H, dq, J=7.0Hz, 14.0Hz), 3.98-4.00(1H, m), 7.18-7.31(5H, m) |
| 5a | (270MHz)0.37(3H, t, J=7.1Hz), 0.91(1H, dd, J=4.9Hz, 9.1Hz), 1.11(3H, t, J=7.1Hz), 1.45(3H, d, J=6.6Hz), 1.61(1H, dd, J=4.9Hz, 6.6Hz), 1.95(1H, ddd, J=6.6Hz, 9.1Hz, 9.6Hz), 2.96-3.75(5H, m), 7.26(5H, m) |
| 5b | (100MHz)0.36(3H, t, J=7.0Hz), 0.84-1.20(7H, m), 1.54-2.08(4H, m), 2.68-3.88(4H, m), 7.27(5H, m) |
| 10a | (500MHz)0.69(3H, t, J=7.0Hz), 1.11(3H, t, J=7.0Hz), 1.48-1.52(3H, m), 1.51(3H, d, J=6.5Hz), 3.18(1H, dq, J=7.0Hz, 14.0Hz), 3.23(1H, dq, J=7.0Hz, 14.0Hz), 3.33-3.38(1H, m), 3.45(1H, dq, J=7.0Hz, 14.0Hz), 3.49(1H, dq, J=7.0Hz, 14.0Hz), 7.20-7.32(5H, m) |
| 10b | (500MHz)0.69(3H, t, J=7.0Hz), 1.04(3H, t, J=7.5Hz), 1.11(3H, t, J=7.0Hz), 1.47-1.71(4H, m), 1.98-2.04(1H, m), 3.12-3.26(3H, m), 3.45-3.53(2H, m), 7.20-7.32(5H, m) |
| 6a | (400MHz)0.82(3H, t, J=7.3Hz), 1.09(1H, dd, J=4.9Hz, 6.8Hz), 1.13(3H, t, J=7.3Hz), 1.19(3H, d, J=6.4Hz), 1.24(1H, ddd, J=6.8Hz, 8.8Hz, 9.3Hz), 1.42(1H, dd, J=4.9Hz, 8.8Hz), 2.55(1H, dq, J=6.4Hz, 9.3Hz), 3.22-3.60(4H, m) |
| 6b | (500MHz)0.81(3H, t, J=7.0Hz), 0.95(3H, t, J=7.5Hz), 1.11-1.15(4H, m), 1.17-1.30(1H, m), 1.45-1.55(2H, m), 1.59-1.67(1H, m), 2.34-2.23(3H, m), 3.26(1H, dq, J=7.0Hz, 14.0Hz), 3.29(1H, dq, J=7.0Hz, 14.0Hz), 3.45(1H, dq, J=7.0Hz, 14.0Hz, 3.57(1H, dq, J=7.0Hz, 14.0Hz), 7.16-7.29(5H, m) |
| 11a | (400MHz)0.52(3H, t, J=7.0Hz), 1.03(1H, dd, J=4.5Hz, 9.0Hz), 1.10(3H, t, J=7.0Hz), 1.29(3H, d, J=6.5Hz), 1.45(2H, brs), 155(1H, dd, J=4.5Hz, 6.5Hz), 1.66(1H, ddd, J=6.5Hz, 8.5Hz, 9.0Hz), 2.67(1H, dt, J=6.5Hz, 8.5Hz), 3.04(1H, dq, J=7.0Hz, 14.0Hz), 3.15(1H, dq, J=7.0Hz, 14.0Hz), 3.52(1H, dq, J=7.0Hz, 14.0Hz), 3.59(1H, dq, J=7.0Hz, 14.0Hz), 7.17-7.31(5H, m) |
| 11b | (400MHz)0.52(3H, t, J=7.0Hz), 1.00(3H, t, J=7.0Hz), 1.00-1.05(1H, m), 1.44-1.53(1H, m), 1.59-1.61(3H, m), 1.71-1.83(2H, m), 2.45-2.52(1H, m), 3.04(1H, dq, J=7.0Hz, 14.0Hz), 3.11(1H, dq, J=7.0Hz, 14.0Hz), 3.53-3.62(2H, m), 7.17-7.30(5H, m) |
| 7a | (400MHz)0.92(3H, t, J=7.3Hz), 1.05(1H, dd, J=5.9Hz, 6.4Hz), 1.10(3H, t, J=7.3Hz), 1.60(1H, ddd, J=6.4Hz, 9.3Hz, 10.7Hz), 1.73(3H, d, J=6.6Hz), 1.85(1H, dd, J=5.9Hz, 9.3Hz), 2.79(1H, dq, J=6.6Hz, 10.7Hz), 3.25-3.50(4H, m), 7.17-7.31(5H, m), 8.99(3H, brs) |
| 7b | (400MHz)0.90(3H, t, J=7.3Hz), 1.10(7H, m), 1.49(1H, ddd, J=6.4Hz, 8.8Hz, 9.8Hz), 1.92(1H, dd, J=5.9Hz, 8.8Hz), 2.11(1H, m), 2.36(1H, m), 2.62(1H, ddd, J=4.9Hz, 9.8Hz, 9.8Hz), 3.24-3.47(4H, m), 7.19-7.31(5H, m), 9.03(3H, brs) |
| 12a | (500MHz)0.75(3H, t, J=7.0Hz), 1.09(3H, t, J=7.0Hz), 1.55(1H, dd, J=5.5Hz, 5.5Hz), 1.60-1.70(2H,m), 1.65(3H, d, J=6.5Hz), 3.21-3.30(2H, m), 3.35-3.50(3H, m), 7.19-7.29(5H, m), 8.58(3H, brs) |
| 12b | (500MHz)0.75(3H, t, J=7.0Hz), 1.09(3H, t, J=7.0Hz), 1.20(3H, t, J=7.5Hz), 1.51-1.59(2H, m), 1.72-1.74(1H, m), 1.94-2.03(1H, m), 2.26-2.31(1H, m), 3.16-3.28(3H, m), 3.39(1H, dq, J=7.0Hz, 14.0Hz), 3.43(1H, dq, J=7.0Hz, 14.0Hz), 7.18-7.30(5H, m), 8.55(3H, brs) |
| 4c | (500MHz)0.93(3H, t, J=7.0Hz), 1.05(1H, dd, J=6.0Hz), 1.14(3H, t, J=7.0Hz), 1.26(1H, ddd, J=6.5, 9.0, 9.0Hz), 1.39-1.70(5H, m), 3.12-3.17(1H, m), 3.32-3.55(4H, m), 7.18-7.30(5H, m), 5.41(1H, s) |
| 4d | (500MHz)0.90-0.94(9H, m), 1.04(1.H, dd, J=5.5 7.0Hz), 1.14(3H, t, J=7.0Hz), 1.24(1H, ddd, J=7.0, 9.0, 9.0Hz), 1.37(1H, ddd, J=5.0, 8.5, 13.5Hz), 1.61(1H, ddd, J=5.0, 8.5, 13.5Hz), 1.88(1H, m), 3.20(4H, m), 5.42(1H, s), 7.18-7.29(5H, m) |
| 5c | (500MHz)0.37(3H, t, J=7.0Hz), 0.93-0.98(4H, m), 1.12(3H, t, J=7.0Hz), 1.43-1.51(1H, m), 1.53-1.60(1H, m), 1.66(1H, dd, J=5.5Hz), 1.72-1.77(2H, m), 1.96(1H, ddd, J=5.5, 9.5, 10.0Hz), 2.90(1H, dt, J=7.0, 14.0Hz), 3.17(1H, dq, J=7.0, 14.0Hz), 3.53(1H, dq, J=7.0, 14.0Hz), 3.71(1H, dq, J=7.0, 14.0Hz), 7.20-7.32(5H, m) |
| 5d | (500Mhz)0.37(3H, t, J=7.0Hz), 0.92(3H, d, J=6.5Hz), 0.95(1H, dd, J=5.0, 9.5Hz), 0.97(3H, d, J=6.5Hz), 1.12(3H, t, J=7.0Hz), 1.54(1H, ddd, J=4.5, 9.0, 14.0Hz), 1.65(1H, dd, J=5.0, 6.5Hz), 1.74(1H, ddd, J=5.0, 9.5, 14.0Hz), 1.83-1.90(1H, m), 1.96(1H, ddd, J=6.5, 9.5, 9.5Hz), 2.92(1H, ddd, J=4.5, 9.5, 9.5Hz), 3.03(1H, dq, J=7.0, 14.0Hz), 3.16(1H, dq, J=7.0, 14.0Hz), 3.53(1H, dq, J=7.0, 14.0Hz), 3.71(1H, dq, J=7, 14.0Hz), 7.20-7.32(5H, m) |
| 6c | (500MHz)0.82(3H, t, J=7.0Hz), 0.93(3H, t, J=7.0Hz), 1.11-1.14(4H, m), 1.22-1.27(1H, m), 1.36-1.58(5H, m), 2.42-2.48(1H, m), 2.50(2H, brs), 3.24-3.32(2H, m), 3.44(1H, dq, J=7.0Hz, 14.0Hz), 3.56(1H, dq, J=7.0Hz, 14.0Hz), 7.16-7.29(5H, m) |
| 6d | (500MHz)0.82(3H, t, J=7.0Hz), 0.88(3H, d, J=6.5Hz), 0.93(3H, d, J=6.5Hz), 1.11(1H, dd, J=5.5, 7.0Hz), 1.13(3H, t, J=7.0Hz), 1.22(1H, ddd, J=7.0, 9.0, 9.0Hz), 1.33-1.47(3H, m), 1.74-1.81(1H, m), 2.09(2H, brd), 2.46(1H, ddd, J=5.0, 9.0, 9.0Hz), 3.28(1H, dq, J=7.0, 14.0Hz), 3.1(1H, dq, J=7.0, 14.0Hz), 3.44(1H, dq, J=7.0, 14.0Hz), 3.57(1H, dq, J=7.0, 14.0Hz), 7.17-7.29(5H, m) |
| 7c | (500MHz)0.90(3H, t, J=7.0Hz), 1.06-1.09(1H, m), 1.10(3H, t, J=7.5Hz), 1.44-1.65(3H, m), 1.90(1H, dd, J=5.5Hz, 8.5Hz), 2.11(1H, m), 2.01-2.09(1H, m), 2.24-2.31(1H, m), 2.66-2.71(1H, m), 3.25-3.46(4H, m), 7.20-7.30(5H, m), 9.06(3H, brs) |
| 7d | (500MHz)0.89(3H, t, J=7.0Hz), 0.95(3H, d, J=6.5Hz), 1.08(1H, dd, J=6.5, 12.5Hz), 1.10(3H, t, J=7.0Hz), 1.53(1H, ddd, J=6.5, 9.5, 9.5Hz), 1.88-2.03(3H, m), 2.13-2.19(1H, m), 2.72-2.80(1H, m), 3.29(1H, dq, J=7.0, 14.0Hz), 3.34-3.47(3H, m), 7.19-7.30(5H, m), 9.07(3H, brs) |
| 4e | (500MHz)0.95(3H, t, J=7.0Hz), 1.18(3H, t, J=7.0Hz), 1.24-1.30(1H, m), 1.53-1.59(1H, m), 1.73-1.76(1H, m), 4.25(1H, d, J=9.5Hz), 7.20-7.50(10H, m) |
| 5e | (500MHz)0.18(3H, t, J=7.0Hz), 1.10(3H, t, J=7.0Hz), 1.15-1.27(1H, m), 2.03(1H, dd, J=5.5, 5.5Hz), 2.06-2.15(1H, m), 2.37-2.44(1H, m), 2.92-3.02(1H, m), 3.20-3.28(1H, m), 3.29-3.39(1H, m), 4.30(1H, d, J=9.0Hz), 7.20-7.48(10H, m) |
| 6e | (500MHz)0.00(3H, t, J=7.0Hz), 0.97(1H, dd, |

TABLE 2-continued

| Compound | ¹H-NMR (CDCl₃) δ: |
|---|---|
| | J=4.5, 9.5Hz), 1.08((3H, t, J=7.0Hz), 1.77(2H, brs), 1.80–1.90(2H, m), 2.40–2.45(1H, m), 2.83–2.87(1H, m), 3.10–3.16(1H, m), 3.24–3.28(1H, m), 3.59–(1H, d, J=9.0Hz), 7.10–7.40(10H, m) |
| 7e | (500MHz)0.18(3H, t, J=7.0Hz), 1.01(3H, t, J=7.0Hz), 1.07–1.14(1H, m), 1.81–1.93(1H, m), 2.07–2.17(1H, m), 2.47–2.52(1H, m), 2.87(1H, dq, J=7.0, 14.0Hz), 3.09(1H, dq, J=7.0, 14.0Hz), 3.20(1H, dq, J=7.0, 14.0Hz), 4.03(1H, d, J=10.0Hz), 7.11–7.26(8H, m), 7.58(2H, d, J=7.5(Hz), 8.91(3H, brs) |

TABLE 3

| Compound | ¹H-NMR (CDCl₃) δ: |
|---|---|
| 32a | (500MHz)0.89(3H, t, J=7.0Hz), 1.14(3H, t, J=7.0Hz), 1.17(1H, dd, J=5.5, 6.5Hz), 1.27(3H, t, J=7.0Hz), 1.37(1H, ddd, J=6.5, 8.6, 9.0Hz), 1.63(1H, dd, J=5.5, 8.5Hz), 2.58(1H, dd, J=6.0, 15.0Hz), 2.70(1H, dd, J=7.5(15.0Hz), 3.34(1H, dq, J=14.0, 7.0Hz), 3.35(1H, dq, J=14.0, 7.0Hz), 3.43(1H, dq, J=14.0, 7.0Hz), 3.51(1H, dq, J=14.0, 7.0Hz), 3.62–3.67(1H, m), 4.16(2H, q, J=7.0Hz), 5.40(1H, brs), 7.19–7.30(5H, m) |
| 32b | (500MHz)0.80(3H, t, J=7.0Hz), 1.11(3H, t, J=7.0Hz), 1.25(3H, t, J=7.0Hz), 1.38(1H, ddd, J=6.5, 6.5, 9.0Hz), 1.48(1H, dd, J=5.5, 5.5Hz), 1.57(1H, dd, J=5.5, 9.0Hz), 2.61(1H, dd, J=8.5, 16.0Hz), 2.87(1H, dd, J=4.0, 16.0Hz), 3.25–3.51(4H, m), 3.43(1H, dJ=4.0Hz), 4.15(1H, q, J=7.0Hz), 4.26–4.30(1H, m), 7.19–7.31(5H, m) |
| 33 | (500MHz)0.92(3H, t, J=7.0Hz), 1.05(1H, dd, J=5.5, 6.5Hz), 1.15(3H, t, J=7.0Hz), 1.33(1H, ddd, J=6.5, 8.5, 9.0Hz), 1.71(1H, dd, J=5.5, 8.5Hz), 1.81–1.93(2H, m), 2.61(1H, brs), 3.32–3.53(5H, m), 3.79–3.87(2H, m), 5.83(1H, brs), 7.17–7.35(5H, m) |
| 34 | (400MHz)0.91(3H, t, J=7.0Hz), 1.03(1H, dd, J=5.5, 6.5Hz), 1.13(3H, t, J=7.0Hz), 1.18(9H, s), 1.29(1H, ddd, J=6.5, 8.5, 9.0Hz), 1.70(1H, dd, J=5.5, 8.5Hz), 1.89–2.03(2H, m), 3.23–3.28(1H, m), 3.31–3.46(3H, m), 3.51(1H, dq, J=14.0, 7.0Hz), 4.24(2H, t, J=6.5Hz), 7.20–7.31(5H, m) |
| 35 | (500MHz)0.41(3H, t, J=7.0Hz), 1.06(1H, dd, J=5.0, 9.0Hz), 1.12(3H, t, J=7.0Hz), 1.21(9H, s), 1.59(1H, dd, J=5.0, 6.5Hz), 1.92(1H, ddd, J=6.5, 9.0, 9.5Hz), 1.98–2.13(2H, m), 3.07(1H, dq, J=14.0, 7.0Hz), 3.11–3.15(1H, m), 3.19(1H, dq, J=14.0, 7.0Hz), 3.49(1H, dq, J=14.0, 7.0Hz), 3.67(1H, dq, J=14.0, 7.0Hz), 4.19–4.29(2H, m), 7.21–7.32(5H, m) |
| 36 | (500MHz)0.44(3H, t, J=7.0Hz), 1.13(3H, t, J=7.0Hz), 1.10–1.14(1H, m), 1,58(1H, dd, J=5.5, 6.0Hz), 1.83(1H, brs), 1.87–2.08(3H, m), 3.08(1H, dq, J=14.0, 7.0Hz), 3.18–3.29(2H, m), 3.50(1H, dq, J=14.0, 7.0Hz), 3.65(1H, dq, J=14.0, 7.0Hz), 3.84(2H, t, J=6.0Hz), 7.21–7.33(5H, m) |
| 37 | (500MHz)0.49(3H, t, J=7.0Hz), 1.10(3H, t, J=7.0Hz), 1.20(1H, dd, J=5.0, 9.5Hz), 1.41(1H, dd, J=5.0, 6.5Hz), 1.68(1H, ddd, J=6.5, 9.5, 9.5Hz), 1.92–1.99(1H, m), 2.03–2.10(1H, m), 2.45(3H, s), 3.09(1H, dq, J=14.0, 7.0Hz), 3.19–3.26(2H, m), 3.46(1H, dq, J=14.0, 7.0Hz), 3.55(1H, dq, J=14.0, 7.0Hz), 4.11–4.16(1H, m), 4.19–4.24(1H, m), 7.22–7.36(7H, m), 7.80(2H, d, J=8.0Hz) |
| 38 | (500MHz)0.41(3H, t, J=7.0Hz), 1.01(1H, dd, J=5.0, 9.5Hz), 1.13(3H, t, J=7.0Hz), 1.54(1H, dd, J=5.0, 6.5Hz), 1.87(1H, ddd, J=6.5, 9.5, 9.5Hz), 2.02–2.11(2H, m), 2.91–2.97(1H, m), 3.02–3.15(3H, m), 3.20(1H, dq, J=14.0, 7.0Hz), 3.50(1H, dq, J=14.0, 7.0Hz), 3.64(1H, dq, J=14.0, 7.0Hz), 7.20–7.31(8H, m), 7.51–7.53(2H, m) |
| 39 | (500MHz)0.83(3H, t, J=7.0Hz), 1.09(1H, dd, J=5.0, 6.5Hz), 1.13(3H, t, J=7.0Hz), 1.20(1H, ddd, J=6.5, 9.5, 9.5Hz), 1.49(1H, dd, J=5.0, 9.0Hz), 1.85–2.01(2H, m), 2.22(2H, brs), 2.54(1H, ddd, J=5.0, 8.0, 9.5Hz), 2.99(1H, ddd, J=6.5, 0.5, 12.0Hz), 3.09(1H, ddd, J=5.5, 9.5, 12.0Hz), 3.28(1H, dq, J=14.0, 7.0Hz), 3.31(1H, dq, J=14.0, 7.0Hz), 3.42(1H, dq, J=14.0, 7.0Hz), 3.53(1H, dq, J=14.0, 7.0Hz), 7.17–7.69(10H, m) |
| 40 | (500MHz)0.57(3H, brt, 1.13(3H, t, J=7.0Hz), 1.19–1.34(2H, m), 1.41(9H, s), 1.72–1.78(1H, m), 2.03–2.12(1H, m), 2.32–2.42(1H, m), 2.92(1H, ddd, J=7.0, 9.0, 12.0Hz), 3.01(1H, ddd, J=5.0, 9.5, 12.0Hz), 3.06–3.15(1H, m), 3.27(1H, dq, J=14.0, 7.0Hz), 3.38(1H, dq, J=14.0, 7.0Hz), 3.44–3.52(1H, m), 3.56(1H, dq, J=14.0, 7.0Hz), 4.94(1H, brs), 7.17–7.29(8H, m), 7.47–7.49(2H, m) |
| 41 | (500MHz)0.54(3H, brt, J=7.0Hz), 1.12–1.20(1H, m), 1.13(3H, t, J=7.0Hz), 1.42(9H, s), 1.46–1.50(1H, m), 1,83(1H, dd, J=8.0, 16.0Hz), 3.07(1H, dq, J=14.0, 7.0Hz), 3.32(1H, dq, J=14.0, 7.0Hz), 3.36(1H, dq, J=14.0, 7.0Hz), 3.61(1H, dq, J=14.0, 7.0Hz), 3.80–3.90(1H, m), 4.94(1H, brs), 5.11(1H, d, J=10.5Hz), 5.20(1H, d, J=17.0Hz), 6.03–6.10(1H, m), 7.18–7.30(5H, m) |
| 6f | (500MHz)0.83(3H, t, J=7.0Hz), 1.14(3H, t, J=7.0Hz), 1.15(1H, dd, J=5.5, 6.5Hz), 1.31(1H, ddd, J=6.5, 9.0, 9.5Hz), 1.48(1H, dd, J=5.5, 9.0Hz), 2.14(2H, brd), 2.98(1H, dd, J=6.5, 9.5Hz), 3.29(1H, dq, J=14.0, 7.0Hz), 3.30(1H, dq, J=14.0, 7.0Hz), 3.45(1H, dq, J=14.0, 7.0Hz), 3.57(1H, dq, J=14.0, 7.0Hz), 5.06(1H, d, J=10.5Hz), 5.21(1H, d, J=17.0Hz), 5.97(1H, ddd, J=6.5, 10.5, 17.0Hz), 7.17–7.32(5H, m) |
| 7f | (500Mhz)0.91(3H, t, J=7.0Hz), 1.09(1H, dd, J=6.0, 6.5Hz), 1.11(3H, t, J=7.0Hz), 1.72(1H, ddd, J=6.5, 9.0, 10.0Hz), 1.88(1H, dd, J=6.0, 9.0Hz), 3.20(1H, dd, J=7.0, 10.0Hz), 3.30(1H, dq, J=14.0, 7.0Hz), 3.34–3.49(3H, m), 5.42(1H, d, J=10.5Hz), 5.54(1H, d, J=17.5Hz), 6.35(1H, ddd, J=6.0, 10.5, 17.5Hz), 7.20–7.31(5H, m), 9.20(3H, brs) |

INDUSTRIAL APPLICABILITY

The novel optically active aminoalkylcyclopropane derivative of the present invention, a racemic modification thereof, and a pharmaceutically acceptable acid addition salt of the optically active aminoalkylcyclopropane derivative or racemic modification thereof have remarkably high antagonistic activity with respect to NMDA receptor, as compared to known aminomethylcyclopropane derivatives and is useful as a preventive agent for cerebral infarction and a protective agent against ischemic diseases.

What is claimed is:

1. An optically active compound represented by formula (1), a racemic modification thereof, or a pharmaceutically acceptable acid addition salt of said optically active compound or said racemic modification:

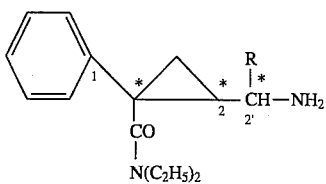 (1)

wherein R is a straight chain or branched $C_1$–$C_5$ aliphatic group which is saturated or unsaturated, or a phenyl group which is unsubstituted or substituted with 1 to 3 substituents which are each independently selected from the group consisting of a halogen atom, a $C_1$–$C_4$ alkyl group, a nitro group, an amino group, a hydroxyl group and a $C_1$–$C_4$ alkoxy group; and mark * indicates an asymmetric carbon atom.

2. The optically active compound, racemic modification thereof, or pharmaceutically acceptable acid addition salt of said optically active compound or racemic modification thereof according to claim 1, wherein R is a $C_1$–$C_5$ alkyl, a $C_2$–$C_5$ alkenyl, or a $C_2$–$C_5$ alkynyl group, which is of a straight chain or branched configuration.

3. The optically active compound, racemic modification thereof, or pharmaceutically acceptable acid addition salt of said optically active compound or racemic modification thereof according to claim 1, wherein R is a phenyl group.

* * * * *